(12) United States Patent
Weisenberg

(10) Patent No.: US 11,033,367 B2
(45) Date of Patent: Jun. 15, 2021

(54) APPARATUS AND METHOD FOR RECORDING DIGITAL IMAGES AND PRESENTING 3D MODELS OF A BODY LUMEN

(71) Applicants: University of Maryland, Baltimore, Baltimore, MD (US); Micah Weisenberg, Frederick, MD (US)

(72) Inventor: Micah Weisenberg, Frederick, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 208 days.

(21) Appl. No.: 15/569,833

(22) PCT Filed: Apr. 29, 2016

(86) PCT No.: PCT/US2016/030052
§ 371 (c)(1),
(2) Date: Oct. 27, 2017

(87) PCT Pub. No.: WO2016/176556
PCT Pub. Date: Nov. 3, 2016

(65) Prior Publication Data
US 2018/0132980 A1    May 17, 2018

Related U.S. Application Data

(60) Provisional application No. 62/154,274, filed on Apr. 29, 2015.

(51) Int. Cl.
*H04N 9/67* (2006.01)
*A61C 9/00* (2006.01)
(Continued)

(52) U.S. Cl.
CPC ........ *A61C 9/0053* (2013.01); *A61B 1/00009* (2013.01); *A61B 1/00091* (2013.01);
(Continued)

(58) Field of Classification Search
CPC ............ A61C 13/0004; A61C 13/0019; A61C 1/0053; A61C 1/0084; A61C 1/0092;
(Continued)

(56) References Cited

U.S. PATENT DOCUMENTS 5,067,899 A * 11/1991 Paschal .............. A61C 17/0202
433/116
6,364,660 B1 * 4/2002 Durbin .................... A61C 9/00
433/213

(Continued)

FOREIGN PATENT DOCUMENTS

| CN | 101536000 A | 9/2009 |
| JP | H0538320 A  | 2/1993 |

(Continued)

OTHER PUBLICATIONS

European Extended Search Report for correspondence EP Application 16787220.9 dated Nov. 14, 2018, pp. 1-8.
(Continued)

*Primary Examiner* — Jayanti K Patel
*Assistant Examiner* — Richard B Carter
(74) *Attorney, Agent, or Firm* — Wolter Van Dyke Davis, PLLC; Eugene J. Molinelli; Cian O'Brien

(57) ABSTRACT

An apparatus including: a lumen scanner (260) configured to scan a body lumen and acquire data for rendering a 3D model of the body lumen. The lumen scanner includes: an optical sensor (240) configured to acquire images of the body lumen while the lumen scanner is disposed inside the body lumen; and a fluid nozzle (202) configured to direct fluid onto an area of the body lumen imaged by the optical sensor while the lumen scanner is disposed inside the body lumen.

20 Claims, 11 Drawing Sheets

(51) Int. Cl.
*B33Y 50/00* (2015.01)
*G06T 19/00* (2011.01)
*A61C 1/05* (2006.01)
*A61B 1/247* (2006.01)
*A61B 1/00* (2006.01)
*A61B 1/015* (2006.01)
*A61B 1/24* (2006.01)
*A61C 13/00* (2006.01)
*A61C 13/34* (2006.01)
*G06F 30/00* (2020.01)

(52) U.S. Cl.
CPC ............... *A61B 1/015* (2013.01); *A61B 1/24* (2013.01); *A61B 1/247* (2013.01); *A61C 1/052* (2013.01); *A61C 13/0004* (2013.01); *A61C 13/0019* (2013.01); *A61C 13/34* (2013.01); *B33Y 50/00* (2014.12); *G06T 19/00* (2013.01); *A61B 1/00016* (2013.01); *A61B 1/00032* (2013.01); *G06F 30/00* (2020.01); *G06T 2210/41* (2013.01)

(58) Field of Classification Search
CPC ..... A61C 1/0052; A61C 9/0053; A61C 1/052; A61C 13/34; A61B 1/00091; A61B 1/0016; A61B 1/00032; A61B 1/015; A61B 1/24; A61B 1/00009; A61B 1/247; A61B 1/00016; B33Y 50/00; B29C 64/386; G06T 19/00; G06T 2210/41; G06F 17/50
USPC ...................... 433/29, 80, 116, 213
See application file for complete search history.

(56) References Cited

U.S. PATENT DOCUMENTS

| | | | |
|---|---|---|---|
| 6,386,867 B1 | 5/2002 | Durbin | |
| 7,494,338 B2 | 2/2009 | Durbin et al. | |
| 8,641,938 B2 | 2/2014 | Howe | |
| 8,989,567 B1 | 3/2015 | Fernandez et al. | |
| 2002/0064752 A1 | 5/2002 | Milford et al. | |
| 2006/0154198 A1* | 7/2006 | Durbin | A61C 9/00 433/29 |
| 2007/0134617 A1 | 6/2007 | Babayoff et al. | |
| 2008/0096161 A1 | 4/2008 | Cain et al. | |
| 2009/0287332 A1 | 11/2009 | Adusumilli et al. | |
| 2012/0261848 A1 | 10/2012 | Haraszati | |
| 2013/0183633 A1 | 7/2013 | Robert et al. | |
| 2013/0293881 A1* | 11/2013 | Tokhtuev | G01N 21/15 356/246 |
| 2013/0316302 A1 | 11/2013 | Fisker | |
| 2014/0272764 A1 | 9/2014 | Miller et al. | |
| 2015/0010882 A1* | 1/2015 | Bergheim | A61C 1/087 433/80 |
| 2016/0239631 A1* | 8/2016 | Wu | A61C 7/002 |
| 2017/0094254 A1 | 3/2017 | Lee et al. | |

FOREIGN PATENT DOCUMENTS

| | | |
|---|---|---|
| JP | 3132673 B2 | 2/2001 |
| JP | 2001258912 A | 9/2001 |
| JP | 2004519289 A | 7/2004 |
| JP | 3132673 U | 6/2007 |
| JP | 2009-297392 A | 12/2009 |
| JP | 2009297392 A | 12/2009 |
| JP | 2014004329 A | 1/2014 |
| JP | 2014-176416 A | 9/2014 |
| JP | 2014176416 A | 9/2014 |

OTHER PUBLICATIONS

ISA/US: International Search Report and Written Opinion, International Patent Application No. PCT/US2016/030052, dated Aug. 8, 2016, pp. 1-10.
Canadian Office Action in correspondence with CA application No. 2984335, dated Aug. 23, 2018, pp. 1-4.
Japanese Office Action in correspondence with JP application No. 2017556819, dated Mar. 6, 2020, pp. 1-8.
ISA/JP: Notice of Reasons for Refusal, issued in corresponding Japan Patent Application No. 2017-556819, dated Mar. 6, 2020, pp. 1-8.

* cited by examiner

APPARATUS AND METHOD FOR RECORDING DIGITAL IMAGES AND PRESENTING 3D MODELS OF A BODY LUMEN

CROSS-REFERENCE TO RELATED APPLICATIONS

This application is a 371 national stage application of PCT Application No. PCT/US16/30052, filed Apr. 29, 2016 which claims benefit of Provisional Application No. 62/154,274, filed Apr. 29, 2015, the entire contents of which are hereby incorporated by reference as if fully set forth herein, under 35 U.S.C. § 119(e).

BACKGROUND

The traditional way of fabricating dentures is a labor intensive process that takes several appointments. The current standard process for complete denture fabrication may include the many steps described in the following.

First, initial impressions of patient's oral cavity are taken during the initial visit. Impressions are poured up with yellow stone to form diagnostic casts. Custom trays are made from patient's casts with a composite or resin base. Custom trays are tried in patient's mouth and adjusted to not extend too far into the soft tissue. Gray stick compound, thermoplastic compound, or viscous impression materials are used to border mold the custom tray, capturing the anatomy of the vestibular depth. The custom trays are filled with impression material and a final impression is taken of the patient's oral cavity. The final impression is boxed and beaded (a technique used to build a wall around the final impression) and the final impression is poured up with green stone for a final cast. Denture bases are made of a composite or resin base from the cast of the final impression. Occlusal rims are made from wax and to standardized measurements. Jaw relations are performed with the occlusal rims in the patient's mouth and are adjusted to he flush. The edges of the rims correspond with the incisal edge. Facebow transfer is done to mount the casts on an articulator. Teeth, denture material, and occlusion design are selected. Wax is removed from the occlusal rims and anterior denture teeth are placed in the maxillary and mandibular arch. Occlusal rims with anterior denture teeth are tried in patient's mouth. Jaw relations are repeated. Wax is removed from occlusal rims and posterior denture teeth are placed in maxillary and mandibular arch. Occlusal rims with anterior and posterior denture teeth are tried in the patient's mouth. Jaw relations repeated. Centric relation is verified. Occlusal rims and record bases are sent off for denture processing. Dentures are delivered to patient and adjusted as needed. As seen from above the current standard process for complete denture fabrication is quite long, complicated, and inconvenient for the patient.

The current standard process for partial denture fabrication may include the many steps described in the following. Initial impressions of patient's oral cavity are taken during the initial visit. Impressions are, poured up with yellow stone to form the diagnostic cast. Framework, tooth selection, and clasp design are determined. Custom trays are made from patient's cast with a composite or resin base. Alterations to teeth for rests and height of contour adjustments are made intra-orally. The custom trays are tried in patient's mouth and adjusted to not extend too far into the soft tissue. Gray stick compound, thermoplastic compound, or viscous impression materials are used to border mold the custom trays. The custom trays are filled with impression material and final impressions are taken of the patient's oral cavity. The final impressions are boxed and beaded (a technique used to build wall around the final impression) and the final impression is poured up with yellow stone for a final cast. The final casts are sent to lab and frameworks are created for each arch. The frameworks are tried in the patient's mouth and adjusted as needed. Occlusal rims are built out of wax on the framework and to standardized measurements. Jaw relations are performed with the occlusal rims in the patient's mouth and are adjusted to be flush. The edge of the rims corresponds with the incisal edge. Facebow transfer is done to mount the casts on an articulator. Wax is removed from the occlusal rims and the teeth are placed. Occlusal rims with denture teeth are tried in the patient's mouth. Jaw relations repeated. Centric relation is verified. The occlusal rims and frameworks are sent off for denture processing. Dentures delivered to patient, adjusted as needed.

The above traditional procedures for complete and partial denture fabrication region five appointments, several materials for each impression, skilled labor to fabricate the denture, and multiple uncomfortable and often messy impressions that are made intra-orally.

Recently, new apparatuses and procedures have been developed to make the denture fabrication process more cost and time effective. For instance, Howe has developed a technology that uses a 3D image of the patient's oral cavity to design a digital version of a denture (U.S. Pat. No. 8,641,938 B2). The record base and occlusal rims are milled from a selected material for jaw relations and then digitally adjusted. A significant portion of the occlusal rim is milled away and a more esthetic material is poured and cured in its place, which is then milled to the contour of teeth.

CAD/CAM designs for both complete and partial dentures exist in the marketplace. "Fused deposition modeling" is a form of 3D printing used for fabricating dentures where microscopic droplets of material are ejected in an x-y plane to build the 3D image of the denture. The denture is created from a 3D model of the denture which requires a 3D image of the patient's oral cavity. However, denture teeth created in this process have low wear resistance. Another form of 3D printing known to those in the art for manufacturing dental prosthetics is stereolithography.

Alternatively, some groups are using computer modeling to design the denture but are only having the denture base milled. These denture bases are often milled with holes corresponding with places for teeth that laboratory technicians place when creating the denture.

Fisker (US Patent Publication No.: 2013/0316302 A1) patented a technique that uses a 3D image of a patient's oral cavity to virtually model and then mill or 3D print the virtual teeth in one material and the gingival portion in another material. The teeth and gingival portion are then connected through unique attachment systems that have been built into the designs of both components.

Avadent® Digital Dental Solutions, of Scottsdale Ariz., currently offers denture fabrication in as little as two visits. During the first visit, the practitioner uses an Anatomical Measuring Device provided by Avadent® to take an impression. The impression is sent to Avadent's® laboratories where it is scanned in and algorithms are used to set the teeth and perform jaw relations. After determining the ideal design, Avadent® mills the record base with corresponding holes for artificial teeth that are placed and bonded or mills the entire denture out a polychromatic material. The denture is polished and inspected by laboratory technicians who compare the final product to the virtual design before sending the denture back to the practitioner for delivery.

Systems that do not obtain border mold and capture the anatomy of the vestibule are considered inferior by many practitioners. Border molding is an essential procedure that allows for customization of the custom tray's peripheral border, which is important to accurately capture the vestibule and ensure optimal denture retention and stability.

The above are all current examples of digital dentures and all require 3D models of the patient's oral cavities. Each technique currently takes a physical impression of patient's oral cavity and then scans that as a negative to develop a 3D model.

Intraoral scanners are currently used to scan teeth prepared for crowns and bridges. Before scanning these preparations, sulcular tissue is often retracted by packing cord soaked in hemodent between the cervical portion of the tooth and the gum tissue, and is removed after ten minutes. This cord is used to create space between the margin of the preparation and the soft tissue in order to better detect the margin of the preparation in the final rendering and create an ideal fitting crown. When scanning margins that are subgingival, obtaining a rendering with clear margins can become especially difficult as the sulcular tissues falls over top of the margin after the retraction cord is removed.

An inability of the current methods and apparati to detect subgingival margins is one of the industry's challenges, and this causes many practitioners to change the way they prepare dental prosthetics. Ideally, in the case of a crown, for example, practitioners seek to position the margin of a crown preparation approximately one (1) mm subgingivally, so that once the crown is placed, the margin is not visible. Because current scanners are not able to scan the subgingival area, when a subgingival scan is necessary, practitioners using intraoral scanners place their margins at or above the gingival margin. As a result, use of intraoral scanners has been relegated to posterior teeth where the margins are not as visible and traditional tooth preparation and impression techniques are used for anterior teeth and more esthetic cases.

Attempts to overcome this deficiency are being made, and include development of radar-like systems to scan through the soft tissue and fluid to detect the margin. However, this is a new and complex endeavor. Accordingly, there is a need for methods and apparatuses that enable a practitioner to easily obtain a rendering with clear margins.

Other times the sulcular tissue is retracted by electrosurgery. Often times, with both electrosurgery and packing retraction cord soaked in hemodent, there can be bleeding. Moisture prevents the practitioner's ability to digitally capture crown margins.

SUMMARY

There is a need for methods and apparati further improving the process of denture fabrication such as to make it less costly, more precise, and more convenient for the patient. A method and apparatus are described herein for recording digital images of a body lumen, such as an oral cavity, to make the presentation of a 3D model, such as the process of denture fabrication, less costly, more precise and more convenient for both a practitioner and the subject whose body lumen in scanned. In some embodiments, the 3D model serves as a design basis for a dental prosthetic or the prosthetic itself.

In a first set of embodiments, an apparatus includes a lumen scanner configured to scan a body lumen and acquire data for rendering a 3D model of the body lumen. The lumen scanner includes: an optical sensor configured to acquire images of the body lumen while the lumen scanner is disposed inside the body lumen; and a fluid nozzle configured to direct fluid onto an area of the body lumen imaged by the optical sensor while the lumen scanner is disposed inside the body lumen.

In a second set of embodiments a system includes: a lumen scanner configured to scan a body lumen and acquire data for rendering a 3D model of the body lumen; and a manufacturing apparatus configured to fabricate a dental prosthetic based on the 3D model. The manufacturing apparatus is selected from a group limited to a milling unit and a 3D printing machine.

In a third set of embodiments, a system includes: a lumen scanner configured to scan a body lumen and acquire data for rendering a 3D model of the body lumen; a source of compressed fluid; and a fluid conduit providing fluid communication between the source of compressed fluid and the fluid nozzle.

In a fourth set of embodiments, a method includes: inserting into a body lumen a lumen scanner having an optical sensor configured to acquire images of the body lumen while the lumen scanner is disposed inside the body lumen; and a fluid nozzle configured to direct fluid onto an area of the body lumen imaged by the optical sensor while the lumen scanner is disposed inside the body lumen; pointing the optical sensor at a portion of the body lumen; directing fluid to the portion of the body lumen at a pressure sufficient to move soft tissue at the portion of the body lumen; and sending signals that indicate data collected by the optical sensor to a processor.

In a fifth set of embodiments, a non-transitory computer-readable medium carries one or more sequences of instructions, wherein execution of the one or more sequences of instructions by one or more processors causes an apparatus to perform the steps of: providing, from an optical sensor in a lumen scanner disposed in a body lumen of a subject, first signals that indicate visible portions of the body lumen and position of the optical sensor and orientation of the optical sensor; receiving second signals that indicates an amount of pressure applied to a fluid in fluid communication with a fluid nozzle disposed adjacent to the optical sensor in the lumen scanner; determining a digital 3D model of the body lumen based on the first signals and the second signals; and presenting on an output device a rendering of the digital 3D model.

For some dental applications, the methods and apparatuses disclosed in this application may improve a practitioners' ability to capture images of subgingival margins by filling the gingival sulcus with a clear fluid, thus maintaining the retraction created by to cord. A dry gas ejected from the fluid nozzles greatly improves a practitioner's ability to control moisture in the region of interest while maintaining separation of the tooth surface and sulcular tissue, allowing for ideal conditions to scan the crown and digitally create a permanent crown.

The foregoing general description and the following detailed description are only examples to provide further explanation.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

Figure 1:
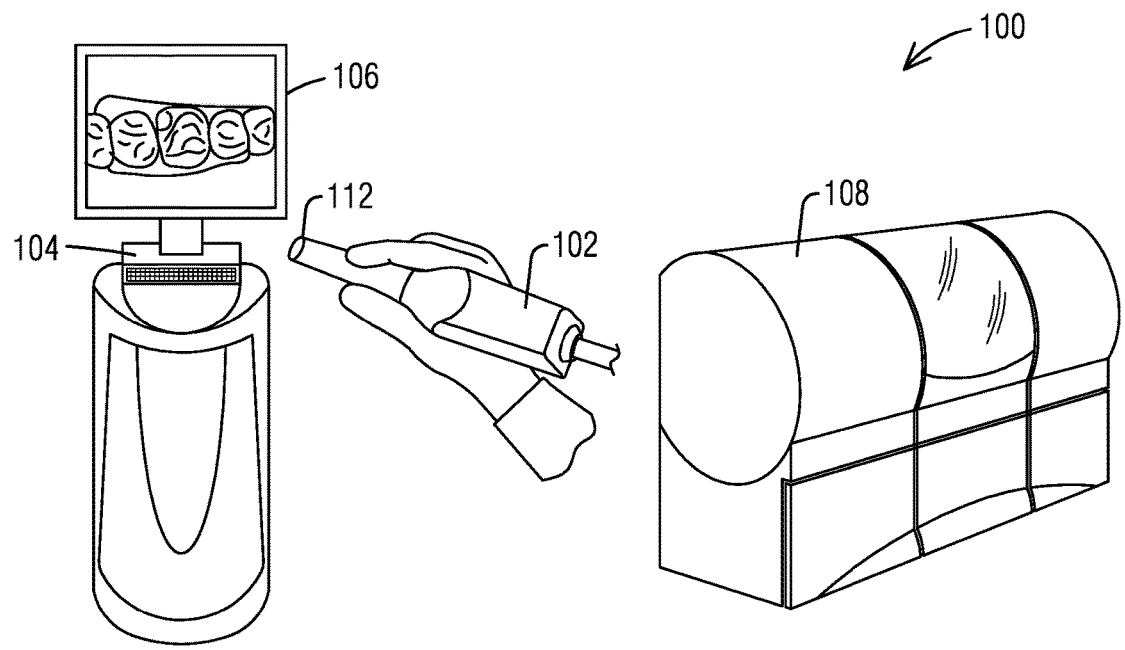
FIG. 1 is an illustration of an example apparatus for recording 3D images of a patient's oral cavity and manufacturing a dental prosthetic using the 3D images, according to the prior art.

A method and apparatus are described for recording digital images of a body lumen, such as a patient's oral cavity or colon, for presenting a 3D model of the body lumen, such as rendering a 3D image or video or 3D printing a positive or negative of a cast or prosthetic or a component of a prosthetic. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Throughout the drawings and the detailed description, unless otherwise described, the same drawing reference numerals are understood to refer to the same elements, features, and structures. The relative size and depiction of these elements may be exaggerated for clarity. Further, it will be understood that when an element is referred to as being "connected to" another element, it can be directly connected to the other element, or intervening elements may be present. The terminology used herein is for the purpose of describing particular embodiments only and is not intended to be limiting of the present disclosure.

Although some features may be described with respect to individual example embodiments, aspects need not be limited thereto such that features from one or more example embodiments may be combinable with other features from one or more example embodiments Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of the fabrication of dental prosthetics such as dentures. However, the invention is not limited to this context. In other embodiments the invention may be used in the context of other dental prosthetics such as crowns and bridges, or to develop 3D models of other lumens in the body of a subject that are inspected with an optical probe, such as endoscopes, colonoscopes, laparoscopes, arthroscopes etc.

1. Overview

Techniques are provided for recording, with an optical sensor in an optical probe, 3D images of a body lumen, such as images of a subject's oral cavity used to fabricate dental prosthetics. In the latter embodiments, the 3D images of an area are obtained using an intraoral scanner that scans the oral cavity via an optical sensor and which takes still images, video images, or a combination of still and video images of the area. The optical probe includes a nozzle that directs a fluid jet that either deflects tissue from the area to be scanned in an amount based on elasticity of the tissue, or further separates soft tissue from a surface covered by the soft tissue, thereby enabling the optical sensor a view of the previously covered surface/area to be scanned. The fluid jet may also keep the area to be imaged clear of seeping intraoral fluids (e.g. blood and saliva), thereby achieving superior isolation of the area. Further, the fluid jets may prevent fluid from splashing back onto the optical sensor.

In many embodiments of the following description, an example body lumen is the oral cavity, and the example fluid is air. In various embodiments the nozzle is in fluid communication with a fluid supply and a source of pressure for the fluid from the supply, such as a gravitational feed, a pump, or a nozzle having a tube and plunger arrangement where the plunger is actuated manually or using a motor. Any liquid or gaseous fluid may serve to displace the soft tissue, such as water or saline etc. However, a clear, gaseous fluid is preferred because it does not interfere with images taken by the intraoral scanner. A dry fluid, such as a gas can eliminate moisture in the lumen. Further, a clear fluid that is harmless to a patient is preferred for both safety and to provide good imaging. In many of the illustrated embodiments, the fluid is air. However, others known in the art may be used, such as high concentrations of oxygen, nitrogen, carbon dioxide, a noble gas etc., alone or in some combination.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

The illustrated devices are 3D intraoral scanners with one or more fluid nozzles, such as air nozzles, embedded or attached. When scanning hard tissue in the intraoral cavity, the device is used in the same fashion as current intraoral scanners. When scanning the soft tissues, especially the vestibule, one or more fluid nozzles blow the fluid at constant or adjustable pressures to provide loading forces and to capture the soft tissue anatomy, such as the oral anatomy previously only obtained through border molding. The fluid pressure is also useful for creating and maintaining retraction of the gingival sulcus when scanning crown margins. In some embodiments, the fluid is dry, e.g., the fluid is a gas that includes water vapor, if any, well below water vapor saturation levels, so that moisture in view of the optical sensor is dried away by the impinging gas.

The scanner is connected either physically or wirelessly to a processor, such as a computer with software, that holds and analyses digital image data obtained by the scanner to render a digital 3D model of the body lumen as an image or other type of output (e.g., a 3D rotatable image or video, a 3D printed output or 3D milled object) based on the 3D model of the body lumen. For example, this 3D model can be used to mill or 3D print a record base, or could supplement other digital denture methods that scan physical final impressions.

The methods and devices disclosed herein may allow, for example, practitioners to develop a 3D digital model of the patient's oral cavity with equivalent or improved detail of a final impression during the initial appointment without using costly and messy impression materials. This method and technology could be used to aid traditional denture making by providing a 3D image of the intraoral cavity from which the record base could be designed and milled, and then having a lab technician develop occlusal rims for jaw relations and eventually manually set the teeth. Alternatively, the method and technology could be used in place of the physical impression for a more advanced digital denture procedure in which a device fabricates a denture base and occlusal rims or the entire denture based on the scan of the oral cavity. Both uses can save materials, labor, and time for both the practitioner and patient.

Further, the methods and apparati disclosed in this application can improve the practitioners' ability to capture subgingival margins, while scanning teeth prepared for crowns and bridges, by filling the gingival sulcus with air, maintaining the retraction created by the cord. Moreover, the air flow from the air nozzles greatly improves the practitioner's ability to control moisture in the region of interest while maintaining separation of the tooth surface and sulcular tissue, allowing for ideal conditions to scan the crown and digitally create a permanent crown. Further, the response of the tissue to the gas pressure, such as forming dimples visible in the images captured by the optical sensor, can indicate the elastic properties of the tissue in the oral cavity or colon or other body lumen.

2. Example Embodiments

FIG. 1 is an illustration of an example apparatus for recording 3D images of a patient's oral cavity and manufacturing a dental prosthetic using the 3D images, according to the prior art. The apparatus includes an intraoral scanner 102, a computer 104 for storing and executing software configured to interpret the data scanned by the intraoral scanner 102, a display 106, and a milling unit 108. Example manufacturers of milling units include: Roland DGA Corp.; Sirona; E4d; Origin; Glidewell Laboratories; Zubler USA; Zirkonzahn USA; Schutz Dental; Jensen Dental; Ivoclar Vivadent; Datron Dynamics; Creo Dental Systems; CadBlu Inc.; B&D Dental Technologies (Origin); Amann Girrbach GmbH; Axsys Dental Solutions; Carestream Dental; Nobel Biocare; and 3M.

In some embodiments, the elements of the apparatus 100 are in wired communication with each other, while in other embodiments the elements are in wireless communication with each other. The intraoral scanner 102 includes at least one optical sensor 112 and is configured to scan the patient's oral cavity and to transmit the data to the computer 104. The computer 104 uses the software to interpret the data and develop a 3D model 110 of the patients' oral cavity. In an embodiment, an image based on the 3D model is shown on the display 106. In an embodiment, the 3D model 110 is used as a 3D design to mill a record base, occlusal rim, or potentially a whole denture. In other embodiments, the 3D model is used by a 3D printer to make a record base, occlusal rim, or the entire denture. Example manufacturers of 3D printers include: EnvisionTec; FormLabs; Javelin Technologies; BEGO; and Stratasys. Example 3D processes include fused deposition modeling and stereolithography.

Figure 2:
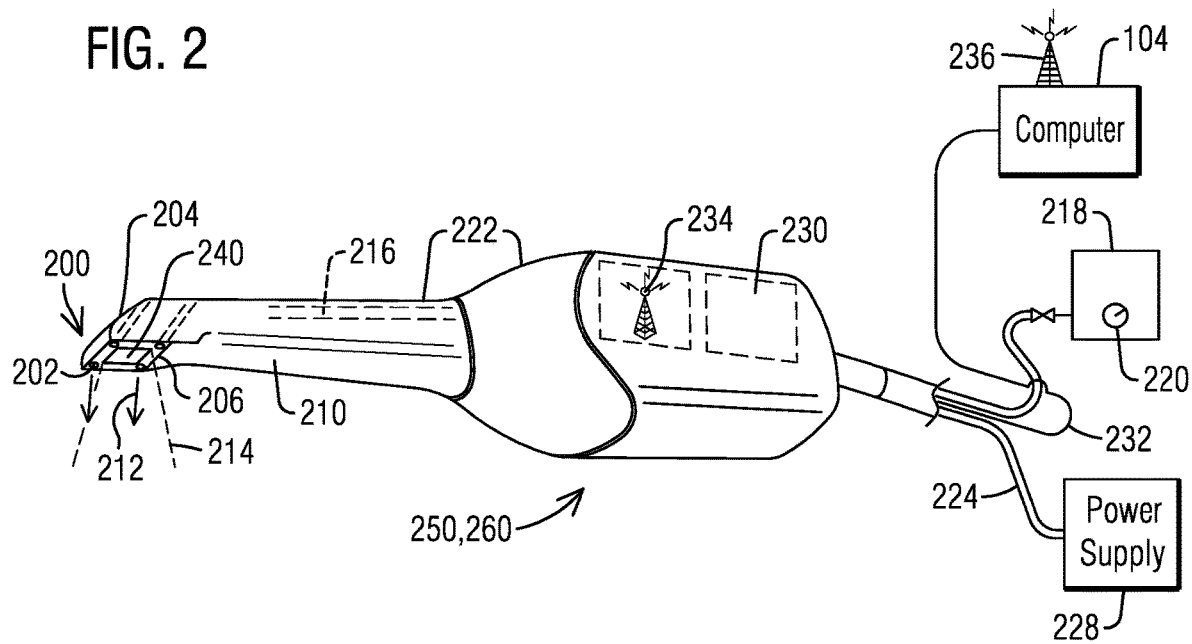
FIG. 2 illustrates an example apparatus for recording 3D images of a patient's oral cavity, including an intraoral scanner, a portable air pressure unit, and a computer, according to one embodiment.

FIG. 2 illustrates an example apparatus 250 for recording 3D images of a patient's oral cavity, including a lumen scanner 260, a pressurized fluid storage unit 218, and a computer 104, according to one embodiment. The lumen scanner 260 includes a fluid nozzle arrangement 200 having at least one fluid nozzle 202. The fluid nozzle 202 is a structure that is configured to generate a flow of fluid that can be delivered onto soft tissue and impart a force sufficient to displace the soft tissue, alone or in combination with other flows. In an embodiment, the structure resembles a simple straight conduit. In another embodiment it may take a more complex shape as necessarily to ensure a threshold amount of collimation of the flow is achieved. Any liquid or gaseous fluid may serve to displace the soft tissue. However, a clear, gaseous fluid is preferred because it does not interfere with images taken by the lumen scanner 260. Further, a clear fluid that is harmless to a patient is preferred. In an embodiment, the fluid is air. However, others known in the art may be used. In this example embodiment, the fluid nozzles 202 are formed integral to a scanner head 204 of the lumen scanner 260. In the illustrated example embodiment there are four (4) fluid nozzles 202 disposed about a perimeter 206 of an optical sensor 240. In this example embodiment, the optical sensor 240 is housed within the scanner head 204. In various embodiments, the optical sensor is a single sensor or an array of sensors, such as a charge couple device (CCD) array in one or two dimensions. However, in some embodiments, the optical sensor 240 protrudes from or is secured to an external surface 210 of the lumen scanner 260. Similarly, in this example embodiment, the fluid nozzles 202 are housed within the scanner head 204. However, in some embodiments, the fluid nozzles 202 protrude from or are secured to an external surface 210 of the lumen scanner 260. The fluid nozzles 202 each eject the fluid in the form of a fluid jet 212 into a field of view 214 of the optical sensor 240. Though FIG. 2 only shows four fluid nozzles 202, a variety of configurations of fluid nozzles 202 could be used, in other embodiments, to displace and stabilize the soft tissue being scanned. Further, in an embodiment, the fluid nozzles 202 are configured to generate parallel fluid jets 212 as shown in FIG. 2. Alternately, the fluid nozzles 202 may be configured to generate fluid jets 212 that converge on each other, or diverge from each other, or some combination, in various other embodiments.

In an embodiment, the lumen scanner 260 includes within its body a fluid conduit 216 feeding the fluid from a pressurized fluid storage unit 218 to the fluid nozzles 202. In an embodiment, the fluid pressure is adjustable to meet the practitioner's specifications via a pressure adjuster 220. The fluid conduit 216 provides fluid communication between the pressurized fluid storage unit 218 and the fluid nozzles 202 and may be at least partly disposed within a housing 222 of the lumen scanner 260. Likewise, a power supply line 224 provides electricity from a power supply 228 and, in an embodiment, is at least partly disposed within the housing 222. Alternately, or in addition, a battery 230 is disposed within the housing to power the lumen scanner 260 when the power supply 228 is not available. In an embodiment, a data communication line 232 provides data communication between the optical sensor 240 and the computer 104. Alternately, or in addition, a wireless transmitter unit 234 is disposed in the housing 222 and transmits the data wirelessly to a wireless receiver unit 236 in data communication with the computer 104, in various other embodiments.

Figure 3:
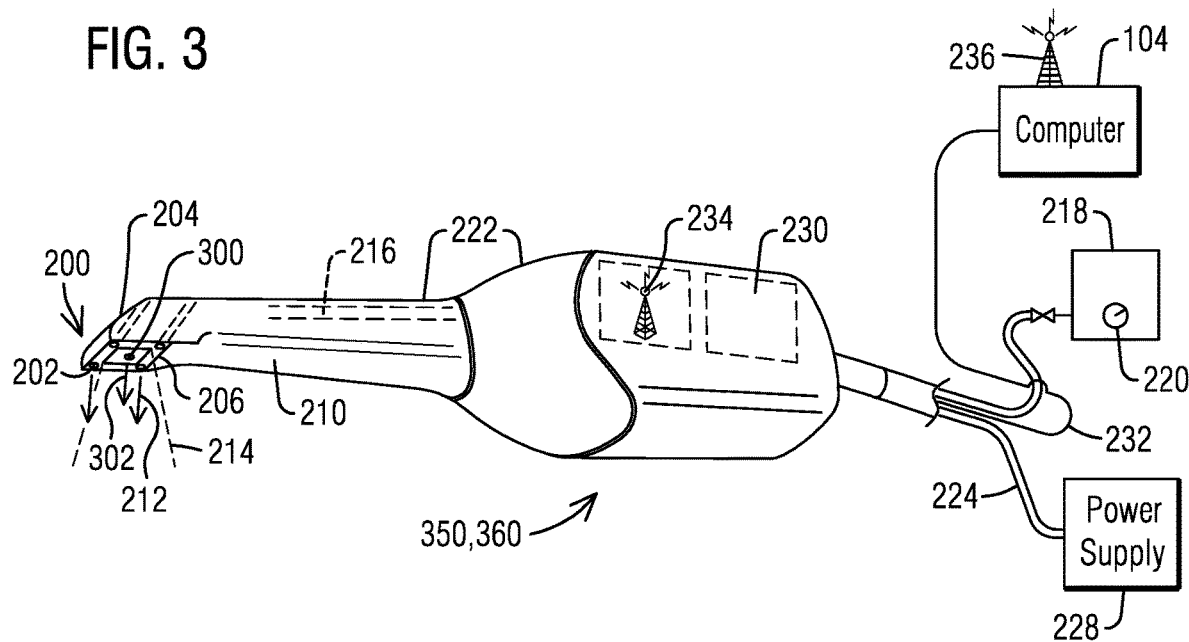
FIG. 3 illustrates an intraoral scanner of an example apparatus for recording 3D images of a patient's oral cavity, according to another embodiment.

FIG. 3 illustrates a lumen scanner 360 of an example apparatus 350 for recording 3D images of a patient's oral cavity, according to another embodiment. In this embodiment, four fluid nozzles 202 are embedded around the perimeter 206 of the optical sensor 240 and an additional fluid nozzle 300 is embedded in the center of the optical sensor 240. Each fluid jet 212 imparts a force on soft tissue at a respective location where it contacts the soft tissue. When there are four parallel fluid jets 212 as in the fluid nozzle arrangement 200 of FIG. 2, the fluid jets 212 can create four dimples in the soft tissue, each dimple associated with a respective fluid jet 212. These four dimples create a raised area of soft tissue between them. The additional fluid nozzle 300 in the center of the optical sensor 240 allows for an additional fluid jet 302 that impinges the soft tissue in the area in between the dimples. This mitigates or prevents the formation of the raised area in between the dimples. This, in turn, enables a smoother contour of the soft tissue in the field of view 214 of the optical sensor 240, which allows for more accurate imaging. In some embodiments, the size or depth of the dimple relative to the pressure of the gas jet is used to estimate the stiffness of the tissue, which can be used to characterize the tissue, e.g., as gum or cheek or healthy or diseased.

Figure 4:
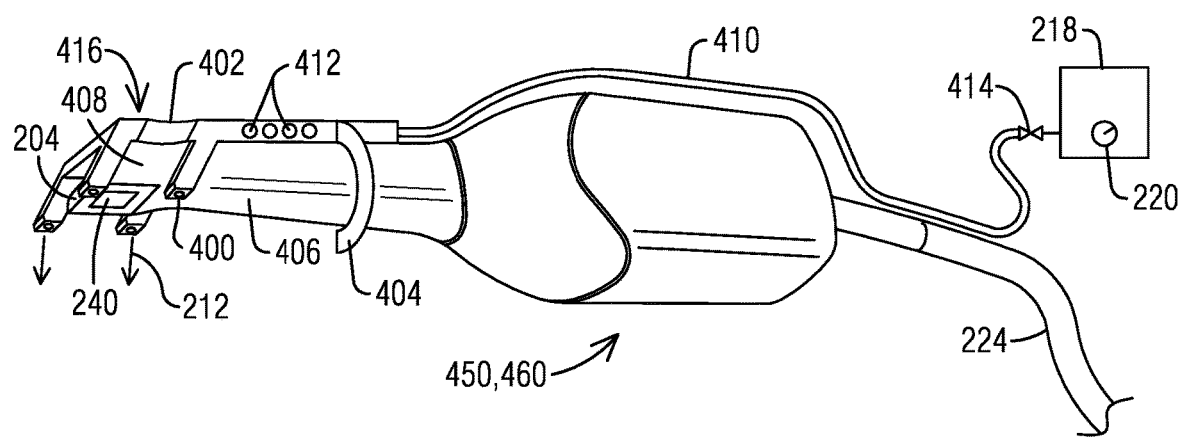
FIG. 4 illustrates an intraoral scanner and a portable air pressure unit of an example apparatus for recording 3D images of a patient's oral cavity, according to yet another embodiment.

FIG. 4 illustrates a lumen scanner 460 and a portable pressurized fluid storage unit 218 of an example apparatus 450 for recording 3D images of a patient's oral cavity, according to yet another embodiment. In this embodiment there are multiple fluid nozzles 400 attached to the lumen scanner 460. The fluid nozzles 400 are connected by an attachment apparatus 402 that is secured to the lumen scanner 460. In an example embodiment the attachment apparatus 402 includes an attachment clip 404 that clips to a neck 406 of the housing 222 yet permits easy removal. The multiple fluid nozzles 400 may be positioned similarly around a tip 408 of the lumen scanner 460. In this embodiment, the fluid conduit 216 is disposed outside the housing 222. For example, a fluid conduit 410 runs along the external surface 210 of the housing 222 between the pressurized fluid storage unit 218 to the fluid nozzles 400. In an embodiment, the fluid nozzles 400 serve a dual role in that they are also configured to clip to the tip 408 of the lumen scanner 460, thereby providing a second securing point. An advantage of this arrangement is that existing scanners can be retrofitted with fluid nozzles. A further advantage is that the fluid nozzles can be made of an inexpensive disposable material. Using inexpensive, disposable materials permits the use of a new nozzle arrangement 200 each time, eliminating the need to sterilize the nozzles for repeated uses.

FIG. 4 further discloses optional individual fluid nozzle controls 412, where each fluid nozzle control 412 controls a flow of fluid to a respective fluid nozzle 400 in an embodiment. This enables individual control of each fluid jet 212, and a main valve 414 provides control of a total fluid flow to the fluid nozzle arrangement 416. The individual fluid nozzle controls 412 and the main valve 414 may be present in any combination in any embodiment. In an example embodiment, select nozzles may have higher pressure air jets to aid in displacement, while other nozzles may have lower air pressure to aid in stabilization of the gingival tissues. Unequal pressures could help stabilize tissue, clear intraoral fluids, and deform tissue uniquely in certain situations.

Previously, an impression taken throughout the mouth has been made with one material that provided a set amount of resistance. One taking the impression could manually apply more pressure in one area than the other, but that leads to displacement of both the tissue and the impression material, which is undesirable. The teachings herein enable the use of various amounts of pressure in different areas of the oral cavity without the detriment associated with the prior art technique, possibly providing fits never before achieved.

In another example embodiment (not shown), instead of individual valves, a control system can include a joystick similar to that of a video game controller. Moving the joystick in a direction can control pressure in a nozzle associated with that direction. For example, pushing to the upper right on the joystick increases pressure for the upper right air nozzle. Pushing the joystick down increases pressures for both of the lower air nozzles. The pressure coming from the air nozzles could also be controlled by software. Depending on the area being scanned and the desired results, the software itself could adjust the air pressures while measuring the results in real time through the intraoral scanner.

With respect to data communication, the configurations in FIG. 2 through FIG. 7 may be set up to be solely wirelessly operated (e.g. cordless) with a battery and wirelessly transmit the obtained data to the computer 104. In some embodiments, the pressurized fluid storage unit 218 is attached to the lumen scanner 460 that is set up to be solely wirelessly operated, making for an especially portable device that provides greater freedom to operate for practitioners.

Figure 5:
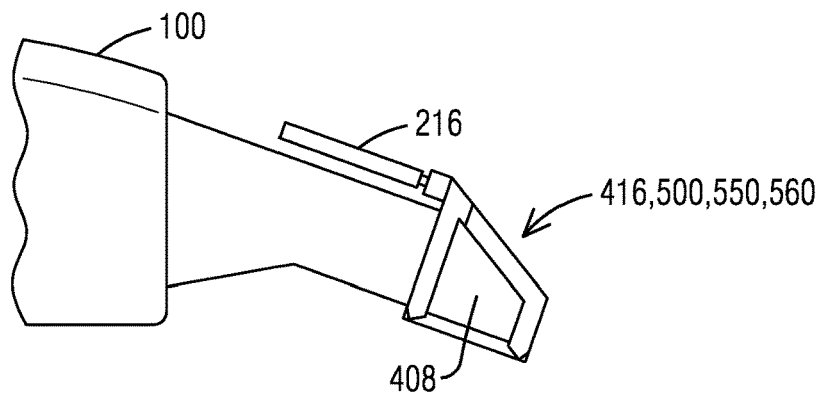
FIGS. 5-7 illustrate an intraoral scanner of an example apparatus for recording 3D images of a patient's oral cavity, according to yet another embodiment.
Figure 6:
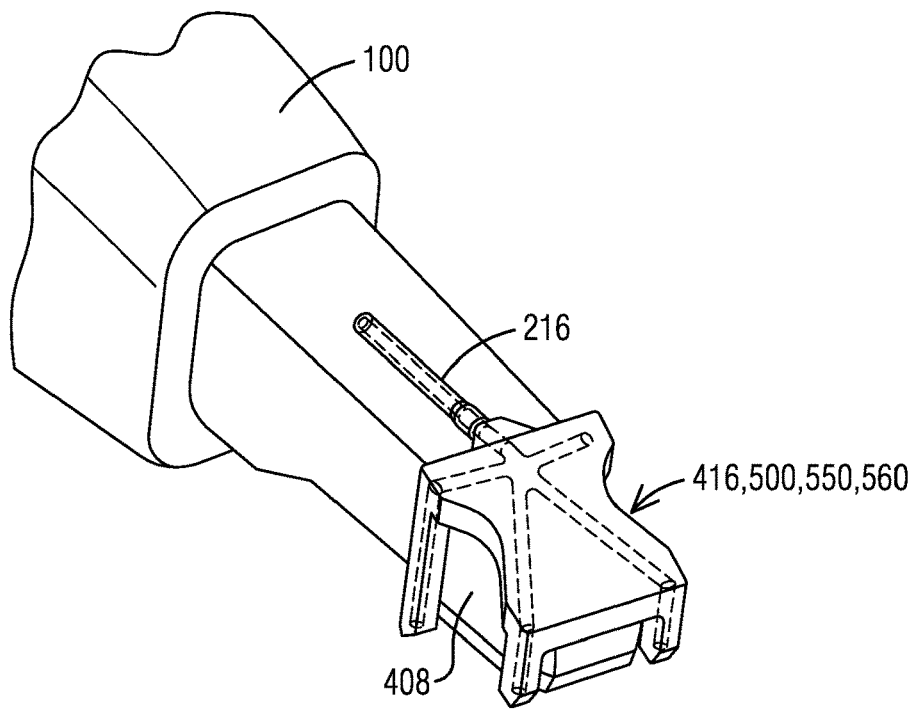
Figure 7:
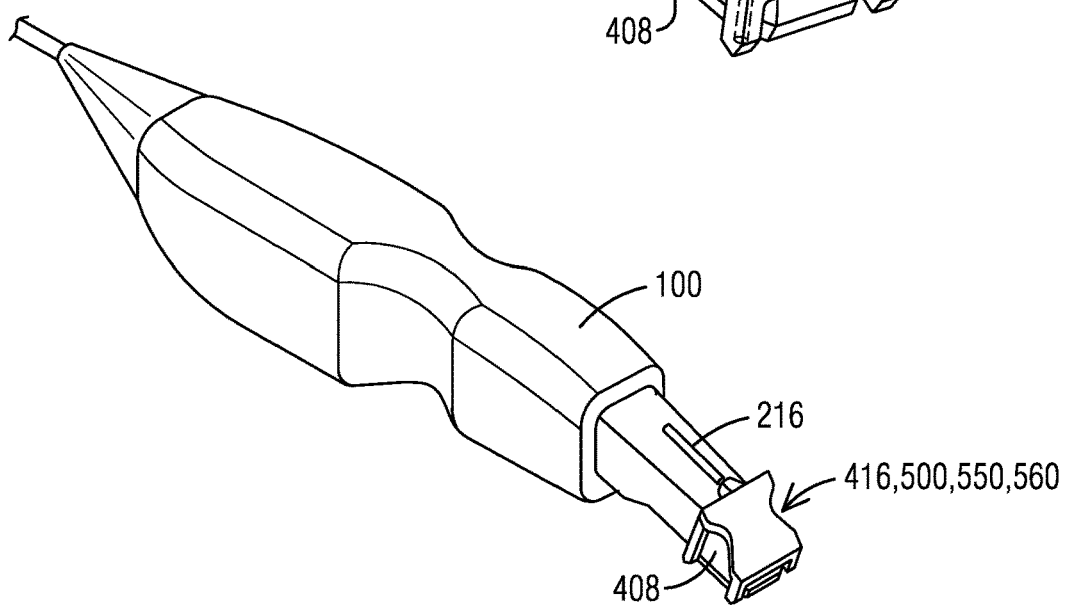

FIG. 5 through FIG. 7 illustrate an intraoral scanner 560 of an example apparatus 550 for recording 3D images of a patient's oral cavity, according to yet another embodiment. In this embodiment, the intraoral scanner is shown with a different housing 222 and a fluid nozzle arrangement 416 external to and removably secured to the tip 408 of the intraoral scanner. A fluid conduit 216 connects to a fluid nozzle head 500. In an embodiment the fluid conduit 216 includes, for example, plastic tubing (e.g. polypropylene) surrounding a rigid (e.g. stainless steel) tube. The fluid conduit 216 is secured to the fluid nozzle head 500 mechanically (e.g. via a press fit or fasteners) and/or chemically (e.g. via an adhesive). The fluid nozzle head 500 is fabricated via methods known to those in the art, including 3D printing processes. The fluid nozzle head 500 is secured to the tip 408 mechanically (e.g. fasteners) or chemically (e.g. via adhesive such as on double sided tape). If an adhesive is used, the adhesive is advantageously strong enough to withstand the forces generated by the fluid jets 212, because the forces tend to urge the fluid nozzle head 500 away from the tip 408. In another example embodiment, the fluid nozzle arrangement 416 combines fluid nozzles 212 that are integral to the housing 222 and those that are external to the housing 222. For example, an integral fluid nozzle 202 may be added in the middle of the optical sensor 240 in the example embodiment shown in FIG. 5 through FIG. 7. Pressurized fluid to the integral fluid nozzle 202 could be supplied by the shown fluid conduit 216 and/or by an additional fluid conduit (not shown) that could be external or internal to the housing 222.

In an example embodiment (not shown), individual nozzles may be primarily responsible for one task and secondarily responsible for another. For example, a select nozzle or nozzles may be primarily responsible for the task of imparting force to move soft tissue and secondarily responsible for the task of preventing fluid from splashing back onto the optical sensor. Likewise, a select nozzle or nozzles of remaining nozzles may be primarily responsible for the task of preventing fluid from splashing back onto the optical sensor and secondarily responsible for the task of imparting force to move soft tissue. This division of roles may be accomplished using embodiments like those seen above, and/or additional nozzles may be added.

In an example embodiment, a nozzle may be located on the perimeter 206 of the optical sensor 240 and may be angled inward toward the optical sensor 240. In such a configuration a fluid jet 212 emanating from the angled nozzle sweeps across the optical scanner, thereby forming an air curtain over the optical sensor 240. The air curtain will entrain fluids that may be splashing back toward the optical sensor 240. Once entrained, the splashed fluids are redirected away from the optical sensor 240 by the air curtain before reaching the optical sensor, leaving the optical sensor 240 free to scan without being unobstructed by the splash back.

In an example embodiment, plural nozzles may be angled inward to contribute to the air curtain nozzle. Ideally, the fluid jets formed by these air curtain nozzles are configured to cooperate with each other on one form or another. For example, each fluid jet may sweep across a respective, different area of the optical scanner such that together the fluid jets cover a wider area than any one jet could by itself. In another example embodiment, the fluid jets may sweep across overlapping areas, but at different distances from the optical sensor 240. In this configuration, the resulting air curtain may be considered thicker, as opposed to wider. In another example embodiment, the fluid jets may be configured to sweep an area that is offset from the optical scanner. For example, if practice indicates that splash back is more likely to come from a certain direction, the fluid jets may be configured to favor sweeping/protecting the optical sensor 240 by forming the air curtain between the optical sensor 240 and the expected origination location of the splash back.

Further, the angle at which the air curtain nozzle is oriented can be selected based on the expected operating environment. In an example embodiment, the angle may be such that the fluid jet sweeps across the optical sensor 240 to form an air curtain that is nearly parallel to the array in the optical sensor 240 and perpendicular to the fluid jets 212 shown in FIG. 4. Alternately, the angle may be such that the fluid jet 212 is closer to normal to the array of the optical sensor 240 and parallel to the fluid jets 212 of FIG. 4. In the former example any splash back may be swept aside, whereas in the latter example any splash back may be pushed back toward its origination location. The former may be more suited for less aggressive splash back coming from any direction, while the latter may be more suited for more aggressive splash back coming from a known direction. Accordingly, the configuration of the air curtain nozzles may be tailored to the expected operated environment.

Figure 8:
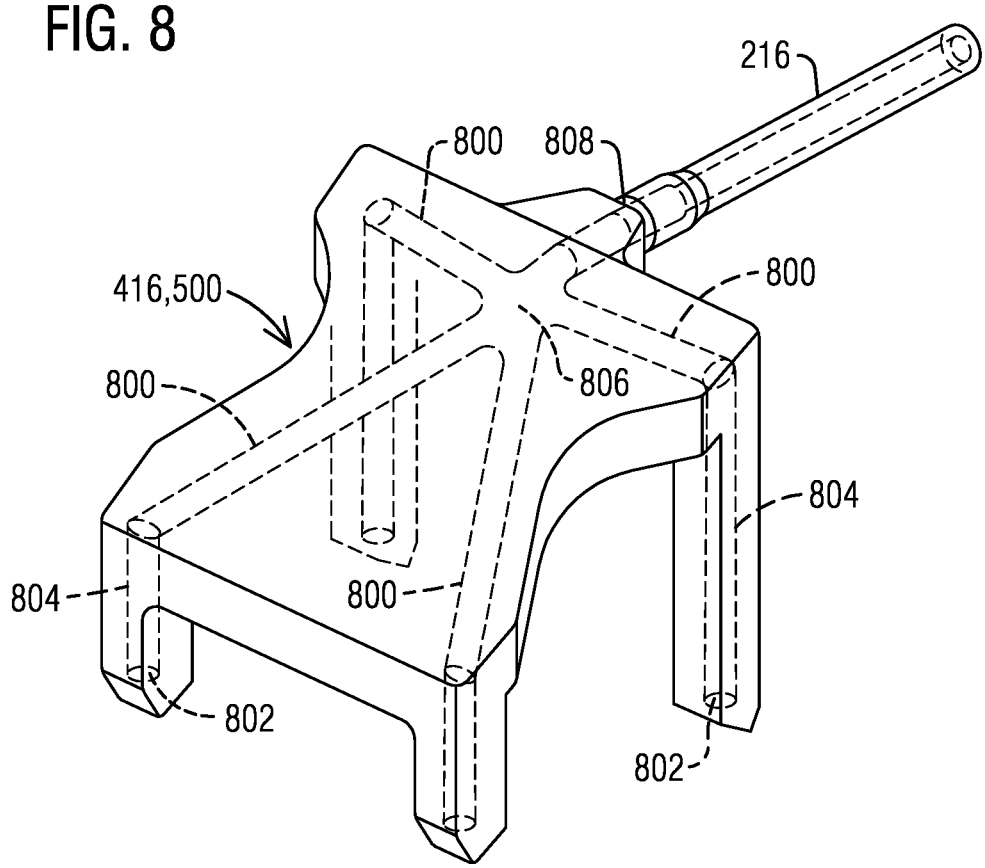
FIGS. 8-9 illustrate an air nozzle arrangement of an example apparatus for recording 3D images of a patient's oral cavity, according to an embodiment.
Figure 9:
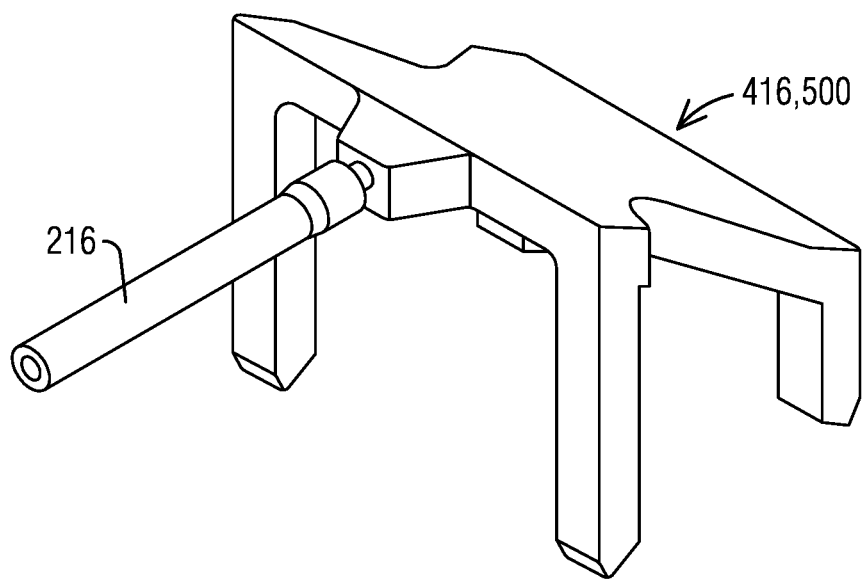

FIG. 8 and FIG. 9 illustrate a fluid nozzle arrangement 416 of an example apparatus 550 for recording 3D images of a patient's oral cavity, according to an embodiment. In this embodiment, the fluid nozzle head 500 and the fluid conduit 216 are separate from the lumen scanner 560. The fluid nozzle head 500 includes internal channels 800, each of which provides fluid communication between the fluid conduit 216 and an outlet 802 of a respective fluid nozzle 804. The internal channels unite upstream at a plenum 806. In an example embodiment the internal channels are designed to have a same pressure drop from an inlet 808 where the fluid conduit 216 connects to the respective outlet 802 or the plenum 806. However, the internal channels 800 may have different lengths and/or different geometries that would otherwise result in different internal pressure drops. To ensure the pressure drops are equal, the internal channels 800 are engineered to include one or more features intended to tailor the pressure drop in the internal channel 800 in an embodiment. For example, an internal channel 800 with a relatively low pressure drop may be made to have a more tortuous path, and/or may include flow obstructions to increase the pressure drop to that of the other internal channels. In this manner the pressure at the outlets 802 can be engineered to be equal. Alternately, the pressures may be differently engineered. Instead, each channel may have a different pressure drop. Uncorrected, this might generate less accurate 3D images, but the fluid nozzle head 500 may be less expensive to manufacture, and the error may be within acceptable parameters. Alternately, the software may be programmed to account for and possibly overcome the optical effect of the local pressure variations and associated different soft tissue deflections. In some embodiments different pressure at each nozzle or jet may be advantageous and thus the corrections, if any, are engineered to provide the advantageous different pressures at each output port.

In an example embodiment the fluid nozzles 804 are oriented parallel to each other, while in another example embodiment the fluid nozzles 804 are canted so the fluid jets 212 converge or diverge. In an example embodiment the fluid jets 212 converge at a single point, considered a focal point. In this example embodiment, the focal point is located at a set distance from the tip 408 of the lumen scanner 560. During operation a practitioner could ensure the tip 408 is set back from the soft tissue to be deflected by approximately the set distance to ensure the focal point approximately coincides with the soft tissue to be deflected. Alternately, the fluid jets 212 are oriented such that they intersect a line oriented normal to an array in the optical sensor 240 and centered in the optical sensor 240, but at different distances from the tip 408. (This line is similar to the trajectory of the fluid jet 212 emanating from the additional fluid nozzle 300 of FIG. 2.) For example, a first fluid jet 212 could intersect the center line at one (1) millimeter, a second fluid jet 212 could intersect the center line at two (2) millimeters, a third fluid jet 212 at three (3) millimeters, and a fourth at four (4) millimeters. In such an embodiment, when the soft tissue to be displaced is disposed along the centerline, the tip 408 could be set apart from the soft tissue by a range of distances (e.g. 1-4 millimeters) and still receive the full displacement force of at least one fluid jet 212. While the displacement force of one fluid jet 212 is less than the displacement force of four jets at the focal point, the focal point is more forgiving in terms of positioning of the tip 408 of the lumen scanner 560. In an example embodiment, not meant to be limiting, forces delivered onto the tissues range from about 0.5 to about 25 kiloNewtons (kN) per square centimeter ($cm^2$). The pressures below about 5 $kN/cm^2$ are advantageous for opening the gingival sulcus (boundary between the base of the enamel and root of the tooth on one side and the gingiva on the other), and the higher pressures in the range are advantageous for moving the cheek away from the gums and moving underlying muscles.

Figure 10A:
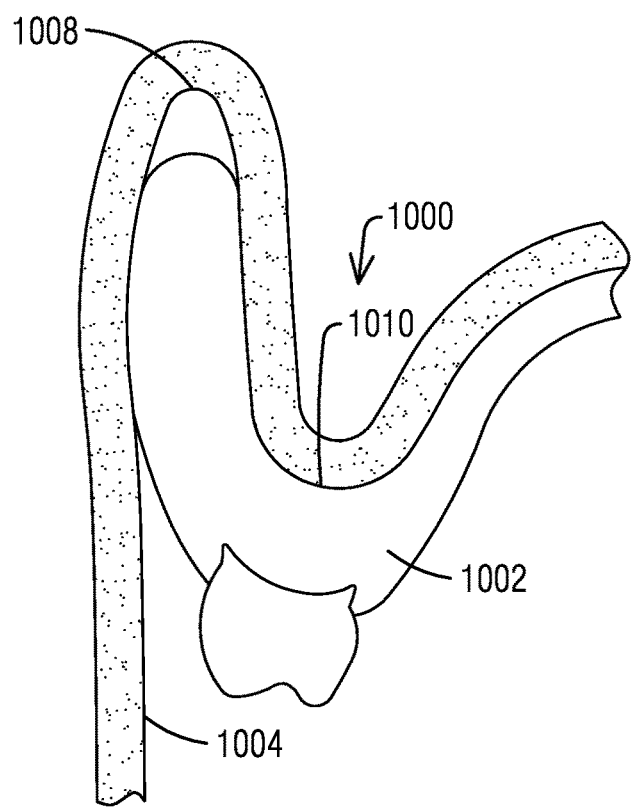
FIG. 10A illustrates a first cross-sectional view of a right side of a maxillary edentulous arch with a denture in place in the coronal plane.
Figure 10B:
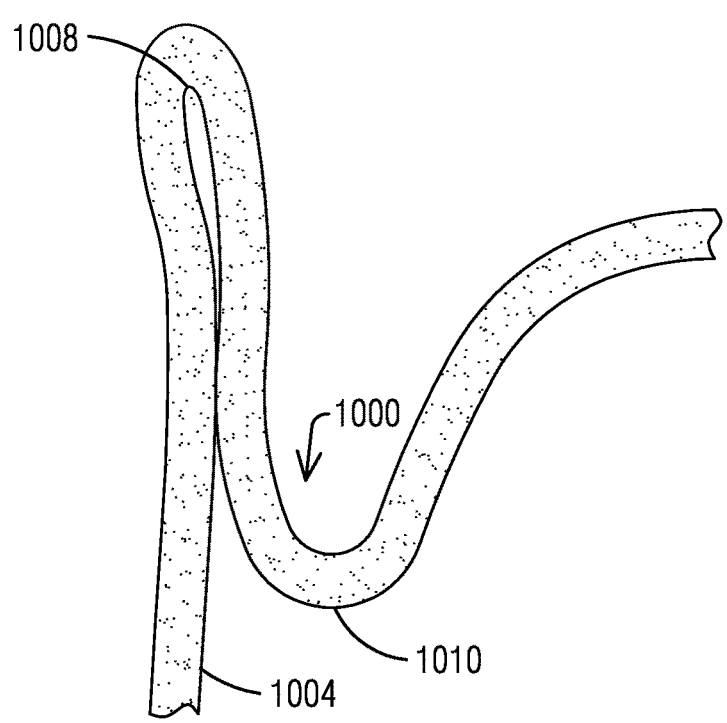
FIG. 10B illustrates another cross-sectional view of the right side of a maxillary edentulous arch in the coronal plane, without the denture in place, to be scanned according to an embodiment.

Methods of using the apparatus for recording 3D images are described hereinafter according to example embodiments of the invention. FIG. 10A illustrates a first cross-sectional view of a right side of a maxillary edentulous arch 1000 with a denture 1002 in place in the coronal plane. FIG. 10B illustrates another cross-sectional view of the right side of a maxillary edentulous arch 1000 in the coronal plane, without the denture 1002 in place, to be scanned according to an embodiment. These figures depict the resting position of the buccal mucosa 1004 with and without the denture 1002 in place in relation to a buccal vestibule 1008 and alveolar ridge 1010. In the absence of fluid nozzle 202, the lumen scanner 560 may be unable to capture the anatomy of the loaded buccal vestibule 1008 because the buccal vestibule 1008 is blocked by the buccal mucosa 1004 and a force is needed to load the soft tissue.

Figure 11:
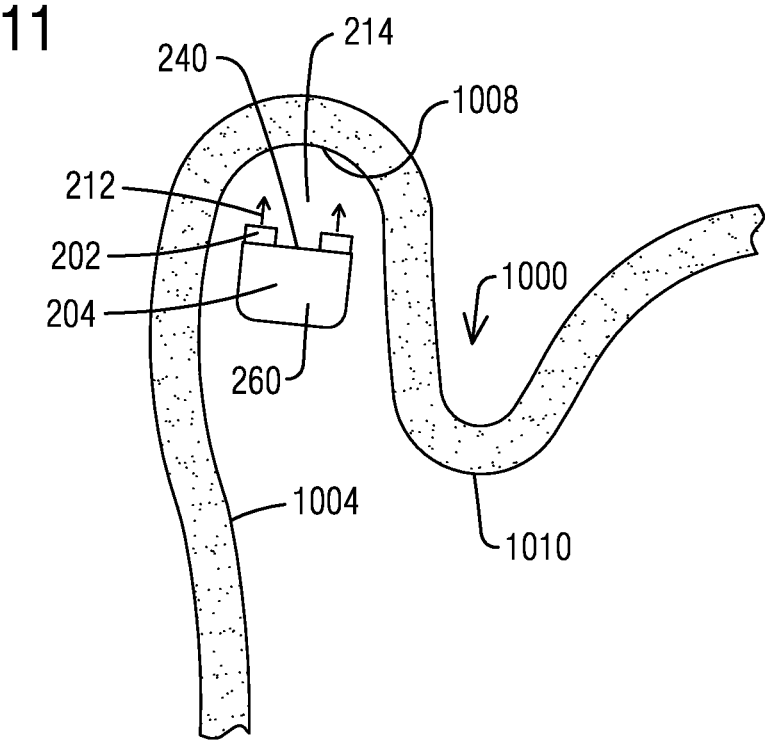
FIG. 11 is a cross-sectional view showing the right side of a maxillary edentulous arch of FIGS. 10A-10B in the coronal plane and action of an intraoral scanner head and air jets in a first position and a first orientation, according to an embodiment.
Figure 12:
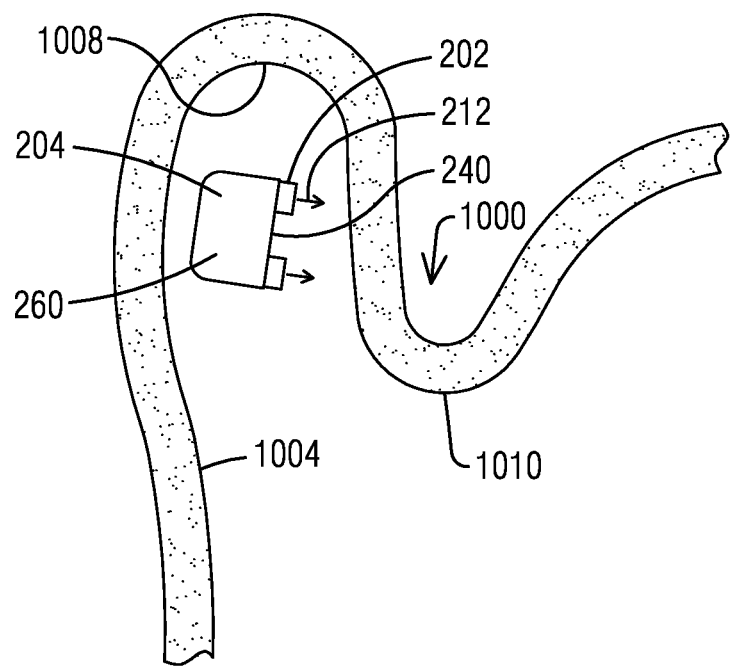
FIG. 12 is the cross-sectional view of FIG. 11 showing action of the intraoral scanner head and air jets in a second position and a second orientation, according to an embodiment.

FIG. 11 is a cross-sectional view showing the right side of a maxillary edentulous arch 1000 of FIGS. 10A-10B in the coronal plane and action of an intraoral scanner head 204 and fluid jets 212 in a first position and a first orientation, according to an embodiment. The fluid nozzles 202 express fluid jets 212 and are being moved along the buccal mucosa 1004 towards the depth of the buccal vestibule 1008. FIG. 12 is the cross-sectional view of FIG. 11 showing action of the intraoral scanner head 204 and fluid jets 212 in a second position and a second orientation, according to an embodiment. The scanner head 204 is rotated from the buccal mucosa 1004 to the alveolar ridge 1010 with fluid being expressed throughout. As the fluid jet 212 is expressed into the buccal vestibule 1008, the unattached tissue is loaded similarly to the way it is loaded during border molding. The fluid pressure may be adjusted, engaging the muscles in the buccal vestibule 1008, which allow for detection of the underlying muscular anatomy. The anatomy is captured by the optical sensor 240 in the scanner head 204, which is scanning the field of view 214.

Figure 13:
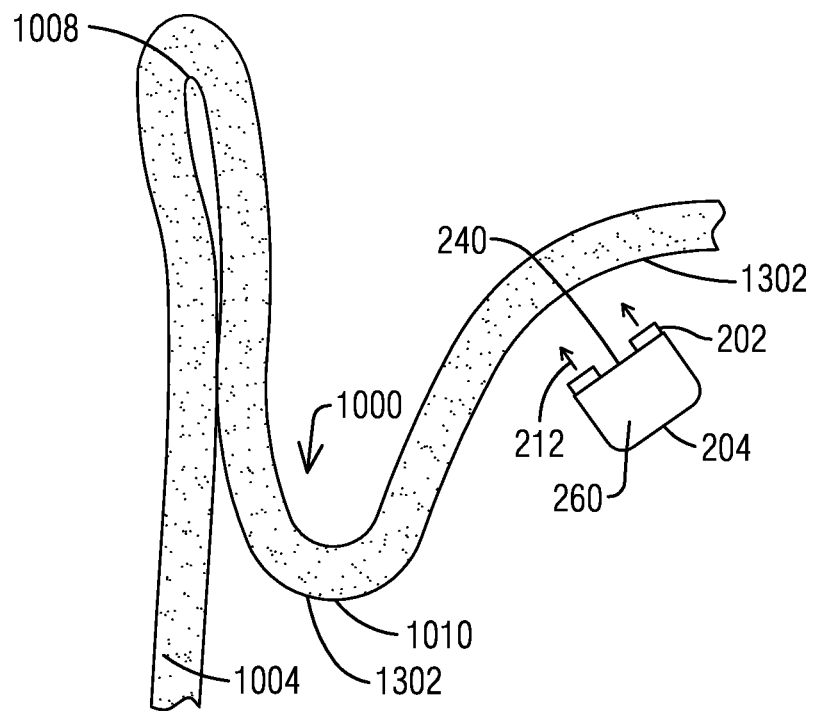
FIG. 13 is the cross-sectional view of FIG. 11 showing action of the intraoral scanner head and air jets in a third position and a third orientation, according to an embodiment.

FIG. 13 is the cross-sectional view of FIG. 11 showing action of the intraoral scanner head 204 and fluid jets 212 in a third position and a third orientation, according to an embodiment. The scanner head 204 is moved coronally along the alveolar ridge 1010 towards a crest 1300 of the alveolar ridge 1010 with fluid jets 212. The practitioner scans the alveolar ridge 1010 for edentulous patients or any teeth in patients that are partially edentulous before moving medially and scanning the soft palate and the hard palate 1302.

In some embodiments, the capture software averages captured images of each specific area to correct for any fluid ripples such that the resulting rendering contains the anatomy obtained in a final impression, making the rendering ideal to mill the record base from.

Figure 14:
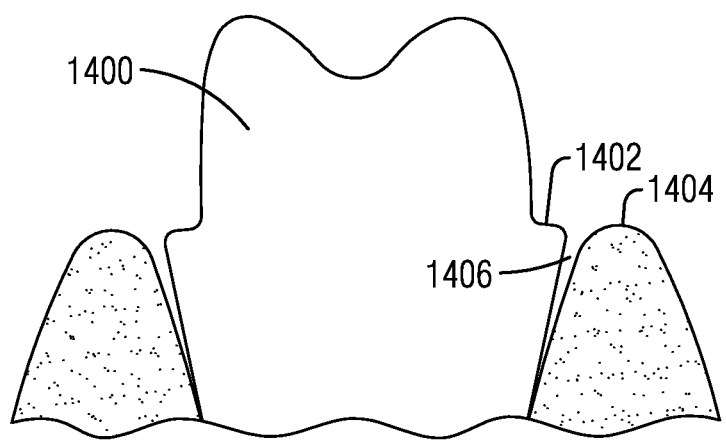
FIG. 14 is a coronal cross sectional view of a molar crown preparation, to be scanned according to an embodiment.
Figure 15:
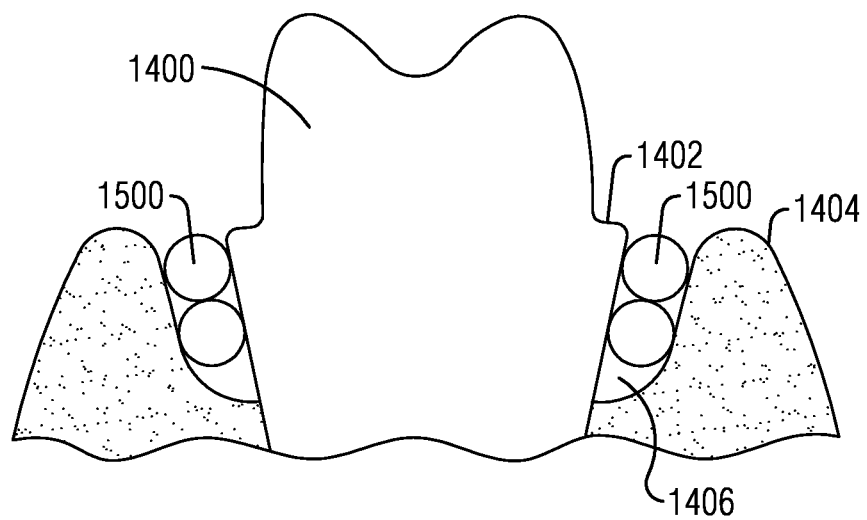
FIG. 15 is the coronal cross sectional view of FIG. 14, showing the molar crown preparation with a packing retraction cord.

Other methods of using the apparatus for recording 3D images (such as the apparatuses shown in FIG. 1 through FIG. 7) are described hereinafter according to an example embodiment of the invention. FIG. 14 is a coronal cross sectional view of a molar crown preparation 1400, to be scanned according to an embodiment. Between a margin 1402 of the crown preparation 1400 and attached gingiva 1404 is the gingival sulcus 1406. Before scanning the crown preparation 1400, space between the margin 1402 of the crown preparation 1400 and the attached gingiva 1404 is created by various methods. A common method for creating said space includes packing the retraction cord 1500 soaked in Hemodent into gingival sulcus. FIG. 15 is the coronal cross sectional view of FIG. 14, showing the molar crown preparation 1400 with the packing retraction cord 1500.

Figure 16:
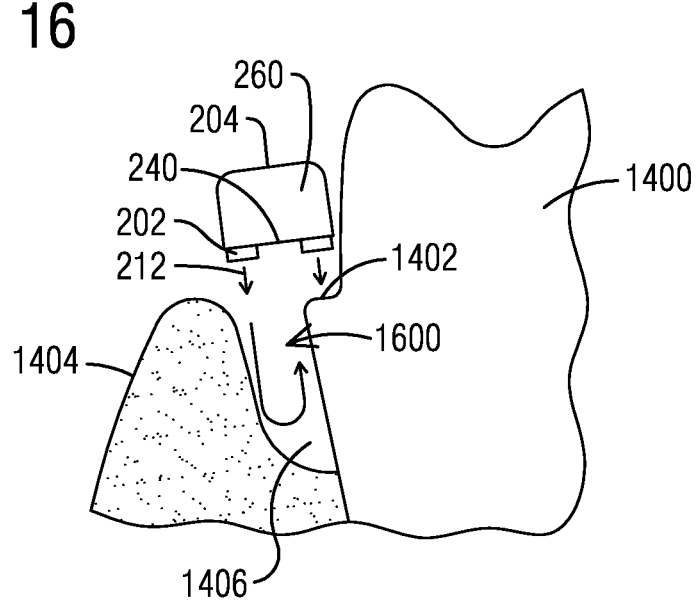
FIG. 16 is a close up of the coronal cross sectional view of FIG. 14, showing the molar crown preparation showing action of the intraoral scanner head and air jets, according to an embodiment.

FIG. 16 is a close up of the coronal cross sectional view of FIG. 14, showing the molar crown preparation 1400 and showing action of the intraoral scanner head 204 and fluid jets 212, according to an embodiment. According to an example embodiment of the invention, a method for creating said crown preparation space includes the use of the lumen scanner 260 with the fluid nozzle 202 used to create fluid jets 212 that flood the gingival sulcus 1406 aiding in maintaining a space 1600 between the crown margin 1402 and the attached gingiva 1404 (as shown in FIG. 16) and helping to control any moisture while the crown preparation 1400 is being scanned by the optical sensor 240. In an example embodiment, both the fluid nozzle arrangement 200 and the retraction cords 1500 may be used as explained above. Alternatively, the force of the fluid jets 212 alone may be enough to create sufficient space 1600 between the crown margin 1402 and the attached gingiva 1404, negating the need for retraction cord 1500 or other space creating methods.

In some embodiments, the crown preparation 1400 is scanned while fluid nozzles 202 are blowing fluid jets 212 at alternating pressures. These various pressures enable the differentiation of soft tissue from hard tissue and bone. For example, while scanning a specific area and directing the fluid jets 212 thereon, there is displacement of the soft tissue and fluid. In an example embodiment, the practitioner holds the lumen scanner 260 in that area for several moments, during which time dozens of images are recorded. The images show continually moving soft tissue as well as hard tissue. Even if the soft/gingival tissue is flapping over hard tissue or bone, e.g. the crown margin 1402, every time the soft tissue moves away, the crown margin 1402 are in the same spot. By evaluating the images, software can determine which tissue is soft tissue and which tissue is hard tissue, and thus provide superior crown margin detection. The amount of deformation allows the user or software to determine the amount of resistance/elasticity in the tissue. Further, the force of the fluid could cause the underlying muscles to engage, resisting displacement. This allows for detection of the underlying muscular anatomy.

In addition, scanning parameters could be adjusted to improve tissue differentiation. For example, a pressure of the fluids in the air jets 212 could be adjusted during the process. A pressure increase, for example, may displace soft tissue that does not move at the lower pressure.

3. Method for Imaging an Oral Cavity

Figure 17:
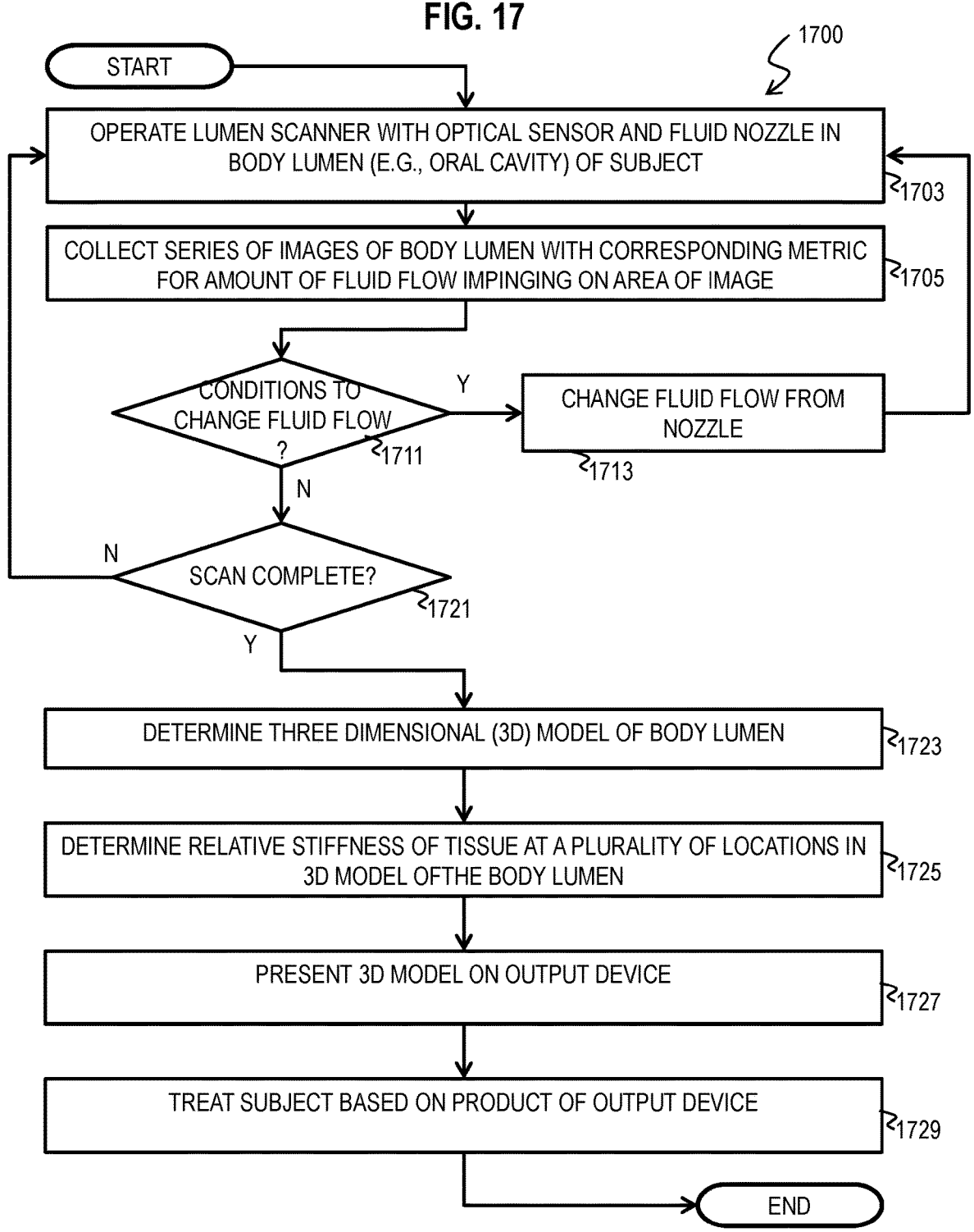
FIG. 17 is flow chart that illustrates an example method for operating and using a 3D scanner with air jets, according to an embodiment.

FIG. 17 is flow chart that illustrates an example method 1700 for operating and using a 3D scanner with fluid jets, according to an embodiment. Although steps are depicted in FIG. 17 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 1703 the lumen scanner is operated in a body lumen by moving the lumen scanner near a portion of a surface (wall) of the body lumen to be imaged by the optical sensor and pointing an optical sensor of the lumen scanner at the portion of the surface of the body lumen and directing fluid through the fluid nozzle at a rate sufficient for imaging purposes, e.g. no flow where the surface is visible or the stiffness of the tissue is not to be determined, at a force sufficient to move a flap of soft tissue to uncover a portion of the surface of the body lumen that otherwise would be covered by the soft tissue, or at a force to move the tissue that constitutes the portion of the surface of the body lumen sufficiently to determine the stiffness of the tissue.

In step 1705, one or more images of the portion of the surface of the body lumen are collected along with data that indicates the position and orientation of the lumen scanner and data that indicates a metric of the fluid flow, such as flow rate or pressure at the nozzle or direction of one or more nozzles or some combination. For example, the image data is collected via wired electronic or wireless electromagnetic communications and the metric of fluid flow is determined by the command signals to an actuator, such as a motor or pump, and a calibration curve that relates the command signal to the metric of fluid flow. In some embodiments, a flow rate or pressure sensor is located at or near the nozzle to provide the metric of fluid flow. The metric of fluid flow is stored in a computer-readable memory in association with the image of the portion of the surface of the body lumen.

In step 1711 it is determined whether conditions are satisfied for changing the fluid flow, e.g. to change the flow rate or pressure or direction of flow. For example, if the practitioner observes that a flap of soft tissue covers the surface to be imaged, e.g., by looking at a screen displaying the current image, then the practitioner determines to increase the amount of fluid flow or change the direction of the fluid flow, e.g., by rotating the lumen scanner, until the image displayed on the screen shows that the soft tissue has been moved to make visible the portion of the surface of the body lumen to be imaged. In the oral cavity embodiments, this corresponds to observing that the buccal vestibule 1008 is blocked by the buccal mucosa 1004 (cheek) and changing the fluid flow or orientation until the buccal mucosa is moved of the buccal vestibule 1008. In some embodiments of the scanning of the oral cavity, it is determined whether the gingival sulcus 1406 (gap) between a margin 1402 of the crown preparation 1400 and attached gingiva 1404 is sufficiently open; and, if not, then changing the orientation or fluid flow rate or pressure to open the gingival sulcus more. In some embodiments, if no soft tissue covers the surface to be imaged, then the fluid flow rate or pressure is reduced.

In some embodiments, if the tissue of the portion of the surface of the body lumen to be imaged is observed to move under the current rate or pressure of fluid flow, then the pressure is decreased until the soft tissue is not moved to determine a stiffness of the tissue L likewise, if the tissue of the portion of the surface of the body lumen to be imaged is not observed to move under the current rate or pressure of fluid flow, then the pressure is increased until the soft tissue begins to move to determine a stiffness of the tissue at that portion of the surface. A change in tissue stiffness requiring a change in the fluid metric (flow rate, pressure or direction or some combination) can indicate a change between healthy and diseased tissue.

If it is determined in step 1711 that conditions are satisfied to change fluid flow, then in step 1713 the fluid flow is changed, by increasing or decreasing the fluid flow rate or pressure or direction or some combination; and control passes back to step 1703 and 1705 to operate the lumen scanner at the portions of the surface of the body lumen and collect more image data and flow metric data. If conditions are not satisfied for changing the fluid flow, then control passes to step 1721.

In step 1721, it is determined whether scan is complete; e.g., all portions of the body lumen to be imaged have been imaged. If not, control passes back to step 1703 to operate the lumen scanner to move it to a new position to image a new portion of the surface of the body lumen. If the scan is complete, then control passes to step 1723.

In step 1723 a three dimensional model of the surface defining the body lumen is determined using any method known in the art. Several commercially available software packages determine the 3D model from the images collected with n the body lumen.

In some embodiments, in step 1725, the stiffness of the tissue along the surface of the 3D model of the body lumen is determined based on the fluid metric involved to move the tissue at the time an image that contributed to the portion of the 3D model was collected. In some embodiments, the stiffness of the tissue along the surface of the 3D model of the body lumen is not determined and step 1725 is omitted.

In step 1727, the 3D model is presented on an output device, e.g., a view from any interior or exterior position is displayed on a screen, or a video of a flight through the body lumen is displayed as video on a screen, or a 3D printer renders a 3D print of the oral cavity or its negative, equivalent to a mold that fills the body lumen.

In step 1729 a subject whose body lumen has been imaged to produce the 3D model is treated based on the product of the output device. For example, a dentures base is milled to fit against one or more portions of the rendering of the 3D model of the surface of the body lumen, or a portion of the body lumen with a stiffness outside a range of healthy tissue is excised or treated with radiation or electrical or chemical ablation.

In some embodiments, one or more steps of method 1700 are performed automatically by a processor. For example, a processor s programmed with instructions that cause an apparatus to, during step 1705, provide from an optical sensor in a lumen scanner disposed in a body lumen of a subject, first signals that indicate visible portions of the body lumen and position of the optical sensor and orientation of the optical sensor and receiving second signals that indicates an amount of pressure applied to a fluid in fluid communication with a fluid nozzle disposed adjacent to the optical sensor in the lumen scanner. During step 1723, the processor causes the apparatus to determine a digital 3D model of the body lumen based on the first signals and the second signals; and, during step 1727, the processor causes the apparatus to determine a digital 3D model of the body lumen based on the first signals and the second signals present on an output device a rendering of the digital 3D model.

4. Computational Hardware Overview

Figure 18:
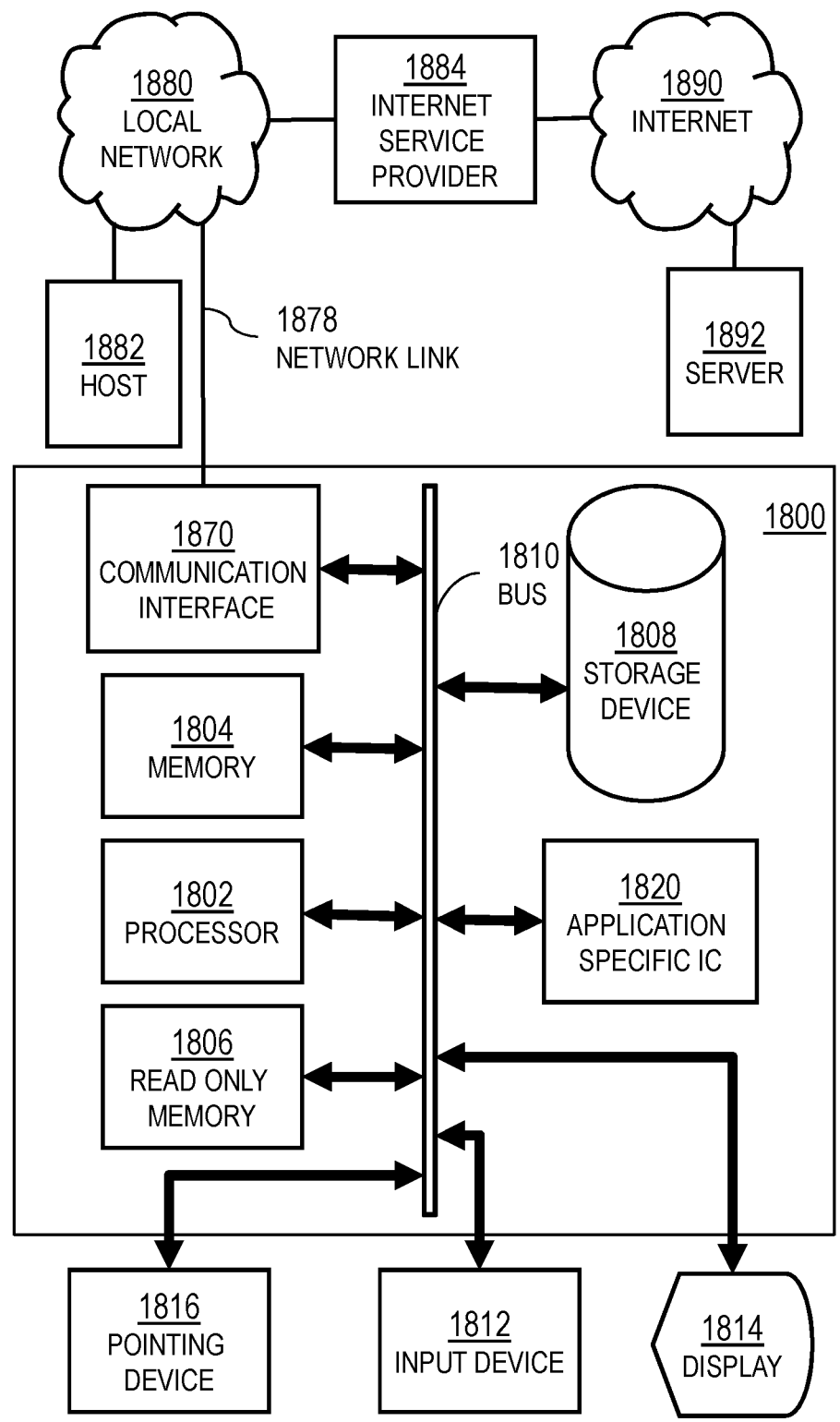
FIG. 18 is a block diagram that illustrates a computer system upon which an embodiment of the invention may be implemented.

FIG. 18 is a block diagram that illustrates a computer system 1800 upon which an embodiment of the invention may be implemented. Computer system 1800 includes a communication mechanism such as a bus 1810 for passing information between other internal and external components of the computer system 1800. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1800, or a portion thereof, constitutes a means for performing one or more steps of one or more methods described herein.

A sequence of binary digits constitutes digital data that is used to represent a number or code for a character. A bus 1810 includes many parallel conductors of information so that information is transferred quickly among devices coupled to the bus 1810. One or more processors 1802 for processing information are coupled with the bus 1810. A processor 1802 performs a set of operations on information. The set of operations include bringing information in from the bus 1810 and placing information on the bus 1810. The set of operations also typically include comparing two or more units of information, shifting positions of units of information, and combining two or more units of information, such as by addition or multiplication. A sequence of operations to be executed by the processor 1802 constitutes computer instructions.

Computer system 1800 also includes a memory 1804 coupled to bus 1810. The memory 1804, such as a random access memory (RAM) or other dynamic storage device, stores information including computer instructions. Dynamic memory allows information stored therein to be changed by the computer system 1800. RAM allows a unit of information stored at a location called a memory address to be stored and retrieved independently of information at neighboring addresses. The memory 1804 is also used by the processor 1802 to store temporary values during execution of computer instructions. The computer system 1800 also includes a read only memory (ROM) 1806 or other static storage device coupled to the bus 1810 for storing static information, including instructions, that is not changed by the computer system 1800. Also coupled to bus 1810 is a non-volatile (persistent) storage device 1808, such as a magnetic disk or optical disk, for storing information, including instructions, that persists even when the computer system 1800 is turned off or otherwise loses power.

Information, including instructions, is provided to the bus 1810 for use by the processor from an external input device 1812, such as a keyboard containing alphanumeric keys operated by a human user, or a sensor. A sensor detects conditions in its vicinity and transforms those detections into signals compatible with the signals used to represent information in computer system 1800. Other external devices coupled to bus 1810, used primarily for interacting with humans, include a display device 1814, such as a cathode ray tube (CRT) or a liquid crystal display (LCD), for presenting images, and a pointing device 1816, such as a mouse or a trackball or cursor direction keys, for controlling a position of a small cursor image presented on the display 1814 and issuing commands associated with graphical elements presented on the display 1814.

In the illustrated embodiment, special purpose hardware, such as an application specific integrated circuit (IC) 1820, is coupled to bus 1810. The special purpose hardware is configured to perform operations not performed by processor 1802 quickly enough for special purposes. Examples of application specific ICs include graphics accelerator cards for generating images for display 1814, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1800 also includes one or more instances of a communications interface 1870 coupled to bus 1810. Communication interface 1870 provides a two-way communication coupling to a variety of external devices that operate with their own processors, such as printers, scanners and external disks. In general, the coupling is with a network link 1878 that is connected to a local network 1880 to which a variety of external devices with their own processors are connected. For example, communication interface 1870 may be a parallel port or a serial port or a universal serial bus (USB) port on a personal computer. In some embodiments, communications interface 1870 is an integrated services digital network (ISDN) card or a digital subscriber line (DSL) card or a telephone modem that provides an information communication connection to a corresponding type of telephone line. In some embodiments, a communication interface 1870 is a cable modem that converts signals on bus 1810 into signals for a communication connection over a coaxial cable or into optical signals for a communication connection over a fiber optic cable. As another example, communications interface 1870 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1870 sends and receives electrical, acoustic or electromagnetic signals, including infrared and optical signals, which carry information streams, such as digital data.

The term computer-readable medium is used herein to refer to any medium that participates in providing information to processor 1802, including instructions for execution. Such a medium may take many forms, including, but not limited to, non-volatile media, volatile media and transmission media. Non-volatile media include, for example, optical or magnetic disks, such as storage device 1808. Volatile media include, for example, dynamic memory 1804. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1802, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1802, except for carrier waves and other signals.

Logic encoded in one or more tangible media includes one or both of processor instructions on a computer-readable storage media and special purpose hardware, such as ASIC 1820.

Network link 1878 typically provides information communication through one or more networks to other devices that use or process the information. For example, network link 1878 may provide a connection through local network 1880 to a host computer 1882 or to equipment 1884 operated by an Internet Service Provider (ISP). ISP equipment 1884 in turn provides data communication services through the public, world-wide packet-switching communication network of networks now commonly referred to as the Internet 1890. A computer called a server 1892 connected to the Internet provides a service in response to information received over the Internet. For example, server 1892 provides information representing video data for presentation at display 1814.

The invention is related to the use of computer system 1800 for implementing the techniques described herein. According to one embodiment of the invention, those techniques are performed by computer system 1800 in response to processor 1802 executing one or more sequences of one or more instructions contained in memory 1804. Such instructions, also called software and program code, may be read into memory 1804 from another computer-readable medium such as storage device 1808. Execution of the sequences of instructions contained in memory 1804 causes processor 1802 to perform the method steps described herein. In alternative embodiments, hardware, such as application specific integrated circuit 1820, may be used in place of or in combination with software to implement the invention. Thus, embodiments of the invention are not limited to any specific combination of hardware and software.

The signals transmitted over network link 1878 and other networks through communications interface 1870, carry information to and from computer system 1800. Computer system 1800 can send and receive information, including program code, through the networks 1880, 1890 among others, through network link 1878 and communications interface 1870. In an example using the Internet 1890, a server 1892 transmits program code for a particular application, requested by a message sent from computer system 1800, through Internet 1890, ISP equipment 1884, local network 1880 and communications interface 1870. The received code may be executed by processor 1802 as it is received, or may be stored in storage device 1808 or other non-volatile storage for later execution, or both. In this manner, computer system 1800 may obtain application program code in the form of a signal on a carrier wave.

Various forms of computer readable media may be involved in carrying one or more sequence of instructions or data or both to processor 1802 for execution. For example, instructions and data may initially be carried on a magnetic disk of a remote computer such as host 1882. The remote computer loads the instructions and data into its dynamic memory and sends the instructions and data over a telephone line using a modem. A modem local to the computer system 1800 receives the instructions and data on a telephone line and uses an infra-red transmitter to convert the instructions and data to a signal on an infra-red a carrier wave serving as the network link 1878. An infrared detector serving as communications interface 1870 receives the instructions and data carried in the infrared signal and places information representing the instructions and data onto bus 1810. Bus 1810 carries the information to memory 1804 from which processor 1802 retrieves and executes the instructions using some of the data sent with the instructions. The instructions and data received in memory 1804 may optionally be stored on storage device 1808, either before or after execution by the processor 1802.

Figure 19:
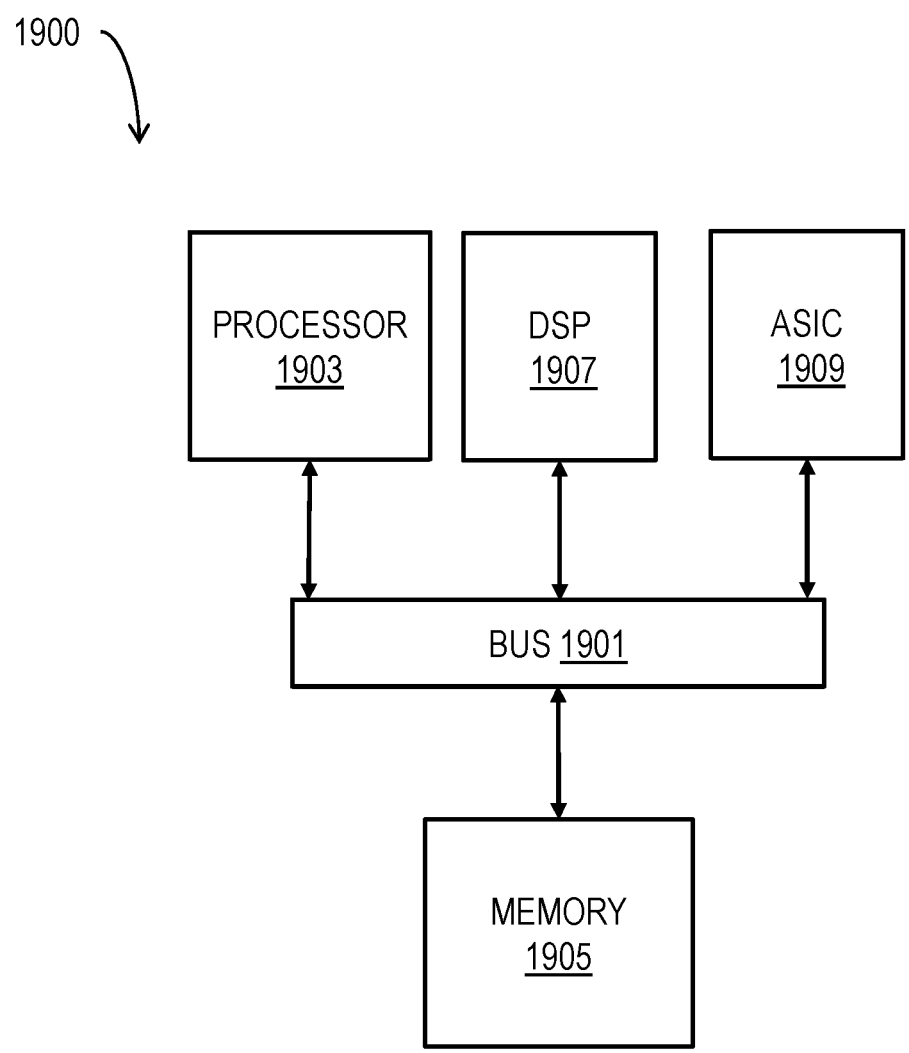
FIG. 19 illustrates a chip set upon which an embodiment of the invention may be implemented.

FIG. 19 illustrates a chip set 1900 upon which an embodiment of the invention may be implemented. Chip set 1900 is programmed to perform one or more steps of a method described herein and includes, for instance, the processor and memory components described with respect to FIG. 18 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1900, or a portion thereof, constitutes a means for performing one or more steps of a method described herein.

In one embodiment, the chip set 1900 includes a communication mechanism such as a bus 1901 for passing information among the components of the chip set 1900. A processor 1903 has connectivity to the bus 1901 to execute instructions and process information stored in, for example, a memory 1905. The processor 1903 may include one or more processing cores with each core configured to perform independently. A multi-core processor enables multiprocessing within a single physical package. Examples of a multi-core processor include two, four, eight, or greater numbers of processing cores. Alternatively, or in addition, the processor 1903 may include one or more microprocessors configured in tandem via the bus 1901 to enable independent execution of instructions, pipelining, and multithreading. The processor 1903 may also be accompanied with one or more specialized components to perform certain processing functions and tasks such as one or more digital signal processors (DSP) 1907, or one or more application-specific integrated circuits (ASIC) 1909. A DSP 1907 typically is configured to process real-world signals (e.g., sound) in real time independently of the processor 1903. Similarly, an ASIC 1909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1903 and accompanying components have connectivity to the memory 1905 via the bus 1901. The memory 1905 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1905 also stores the data associated with or generated by the execution of one or more steps of the methods described herein.

5. Alterations and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. An apparatus comprising:
   a lumen scanner configured to scan a body lumen and acquire data for rendering a 3D model of the body lumen, the lumen scanner comprising:
   an optical sensor configured to acquire images of the body lumen while the lumen scanner is disposed inside the body lumen; and
   a plurality of fluid nozzles configured to direct fluid onto an area of the body lumen imaged by the optical sensor while the lumen scanner is disposed inside the body lumen;
   wherein the plurality of fluid nozzles are positioned around the optical sensor to direct fluid away from the optical sensor and into a field of view of the optical sensor.

2. The apparatus as recited in claim 1, further comprising a housing, wherein the fluid nozzles are incorporated within the housing of the lumen scanner.

3. The apparatus as recited in claim 1, further comprising a housing, wherein the fluid nozzles are attached on the housing of the lumen scanner and is removable from the housing of the lumen scanner.

4. The apparatus as recited in claim 1, further comprising a fluid nozzle control configured to enable control of a fluid pressure of the fluid directed through the fluid nozzles.

5. The apparatus as recited in claim 1, further comprising a portable fluid pressure unit and a fluid conduit connecting the fluid nozzles with the portable fluid pressure unit.

6. The apparatus as recited in claim 1, further comprising a wireless transmission unit configured to wirelessly transmit acquired data to a processor.

7. The apparatus as recited in claim 1, wherein the lumen scanner further comprises:
   a battery;
   a wireless transmission unit configured to wirelessly transmit acquired data to a computer; and
   a portable fluid pressure unit supplying the fluid to the fluid nozzles.

8. The apparatus as recited in claim 1, wherein the lumen scanner comprises a portable fluid pressure unit and a battery to power the lumen scanner.

9. The apparatus as recited in claim 1, wherein the fluid nozzles are configured to generate a fluid flow in the body lumen sufficient to displace soft tissue that obscures hard tissue to be imaged by the optical sensor.

10. The apparatus as recited in claim 9, wherein the plurality of fluid nozzles are disposed about a perimeter of the optical sensor, wherein each fluid nozzle is configured to generate a respective fluid flow aimed into the field of view of the optical sensor.

11. The apparatus as recited in claim 10, wherein the respective fluid flows are parallel to each other.

12. A system comprising:
   the apparatus as recited in claim 1;
   a source of compressed fluid; and
   a fluid conduit providing fluid communication between the source of compressed fluid and the fluid nozzles.

13. The system of claim 12, further comprising a housing to which the optical sensor and the fluid nozzles are secured, wherein the fluid conduit is integrally formed in the housing or is disposed within the housing.

14. The apparatus as recited in claim 1, wherein the fluid nozzles are located on a perimeter of the optical sensor and are angled inward toward the optical sensor so that fluid jets emanating from the fluid nozzles sweep across the optical sensor thereby forming an air curtain over the optical sensor to entrain fluids from being directed back toward the optical sensor.

15. A system comprising:
   the apparatus as recited in claim 1; and
   a manufacturing apparatus configured to fabricate a dental prosthetic based on the 3D model, the manufacturing apparatus selected from a group consisting of a milling unit and a 3D printing machine.

16. A method comprising:
   inserting into a body lumen a lumen scanner comprising an optical sensor configured to acquire images of the body lumen while the lumen scanner is disposed inside the body lumen; and a plurality of fluid nozzles positioned around the optical sensor and configured to direct fluid onto an area of the body lumen imaged by the optical sensor while the lumen scanner is disposed inside the body lumen;

pointing the optical sensor at a portion of the body lumen;

directing fluid, from the plurality of fluid nozzles, to the portion of the body lumen at a pressure sufficient to move soft tissue at the portion of the body lumen; and sending signals that indicate data collected by the optical sensor to a processor.

17. The method of claim 16, wherein directing fluid at a pressure sufficient to move soft tissue further comprises directing fluid, from the plurality of fluid nozzles, at a pressure sufficient to uncover a target portion of the body lumen formerly covered by the soft tissue, and wherein the method further comprises characterizing the soft tissue at the portion of the body lumen based on the movement of the soft tissue at the portion of the body lumen.

18. A non-transitory computer-readable medium carrying one or more sequences of instructions, wherein execution of the one or more sequences of instructions by one or more processors causes an apparatus to perform the steps of:

providing, from an optical sensor in a lumen scanner disposed in a body lumen of a subject, first signals that indicate visible portions of the body lumen and position of the optical sensor and orientation of the optical sensor;

receiving second signals that indicates an amount of pressure applied to a fluid in fluid communication with a plurality of fluid nozzles positioned around the optical sensor in the lumen scanner;

determining a digital 3D model of the body lumen based on the first signals and the second signals; and presenting on an output device a rendering of the digital 3D model.

19. The non-transitory computer-readable medium as recited in claim 18, wherein determining the digital 3D model further comprises not including the first signals in the digital 3D model if it is determined that the amount of pressure or the orientation of the optical sensor or the position of the optical sensor, or some combination, is not sufficient to move soft tissue from covering a target portion of the body lumen.

20. The non-transitory computer-readable medium as recited in claim 18, wherein determining the digital 3D model further comprises determining a relative stiffness of a tissue at a location on the digital 3d model based on the amount of pressure and the visible portions of the body lumen.

* * * * *